United States Patent
Saito

(10) Patent No.: US 10,442,993 B2
(45) Date of Patent: *Oct. 15, 2019

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Masayuki Saito, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 47 days.

This patent is subject to a terminal disclaimer.

(21) Appl. No.: 15/808,846

(22) Filed: Nov. 9, 2017

(65) Prior Publication Data

US 2018/0127651 A1 May 10, 2018

(30) Foreign Application Priority Data

Nov. 10, 2016 (JP) ................................. 2016-219372

(51) Int. Cl.

| | | |
|---|---|---|
| C09K 19/34 | (2006.01) | |
| C07C 13/28 | (2006.01) | |
| C09K 19/30 | (2006.01) | |
| C09K 19/54 | (2006.01) | |
| G02F 1/1337 | (2006.01) | |
| G02F 1/1362 | (2006.01) | |
| C09K 19/06 | (2006.01) | |
| C09K 19/08 | (2006.01) | |
| C09K 19/52 | (2006.01) | |
| C09K 19/04 | (2006.01) | |
| C09K 19/12 | (2006.01) | |

(52) U.S. Cl.
CPC .............. *C09K 19/52* (2013.01); *C07C 13/28* (2013.01); *C09K 19/06* (2013.01); *C09K 19/08* (2013.01); *C09K 19/30* (2013.01); *C09K 19/3001* (2013.01); *C09K 19/3066* (2013.01); *C09K 19/3068* (2013.01); *C09K 19/3402* (2013.01); *C09K 19/54* (2013.01); *C09K 19/542* (2013.01); *G02F 1/1362* (2013.01); *G02F 1/133788* (2013.01); *C07C 2601/18* (2017.05); *C09K 2019/0448* (2013.01); *C09K 2019/122* (2013.01); *C09K 2019/123* (2013.01); *C09K 2019/301* (2013.01); *C09K 2019/3009* (2013.01); *C09K 2019/3027* (2013.01); *C09K 2019/3036* (2013.01); *C09K 2019/3422* (2013.01); *C09K 2019/3425* (2013.01); *C09K 2019/548* (2013.01); *G02F 2001/133742* (2013.01)

(58) Field of Classification Search
None
See application file for complete search history.

(56) References Cited

U.S. PATENT DOCUMENTS

| 2018/0148649 A1* | 5/2018 | Saito ................. C09K 19/2021 |
| 2018/0282624 A1* | 10/2018 | Furusato ............ C09K 19/3066 |

FOREIGN PATENT DOCUMENTS

JP 2014025025 2/2014

* cited by examiner

*Primary Examiner* — Cynthia H Kelly
*Assistant Examiner* — Anna Malloy
(74) *Attorney, Agent, or Firm* — JCIPRNET

(57) ABSTRACT

A liquid crystal composition satisfying at least one of characteristics such as high maximum temperature, low minimum temperature, small viscosity, suitable optical anisotropy and large dielectric anisotropy, or having a suitable balance regarding at least two of the characteristics. The liquid crystal composition contains a quencher as a first additive, and may contain a specific compound having large negative dielectric anisotropy as a first component, a specific compound having high maximum temperature or small viscosity as a second component, or a specific compound having a polymerizable group as a second additive.

15 Claims, No Drawings

LIQUID CRYSTAL COMPOSITION AND LIQUID CRYSTAL DISPLAY DEVICE

CROSS-REFERENCE TO RELATED APPLICATION

This application claims the priority benefit of Japan application serial no. 2016-219372, filed on Nov. 10, 2016. The entirety of the above-mentioned patent application is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having negative dielectric anisotropy, and a liquid crystal display device that includes the composition and has a mode such as an IPS mode, a VA mode, an FFS mode and an FPA mode. The invention also relates to a liquid crystal display device having a polymer sustained alignment mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship in the characteristics. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to a response time in the device. A short response time is preferred for displaying moving images on the device. A shorter response time even by one millisecond is desirable. Accordingly, small viscosity in the composition is preferred. Small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity | Short response time |
| 3 | Suitable optical anisotropy | Large contrast ratio |
| 4 | Large positive or negative dielectric anisotropy | Low threshold voltage, small electric power consumption and large contrast ratio |
| 5 | Large specific resistance | Large voltage holding ratio and large contrast ratio |
| 6 | High stability to ultraviolet light and heat | Long service life |

Optical anisotropy of the composition relates to a contrast ratio in the device. According to a mode of the device, large optical anisotropy or small optical anisotropy, more specifically, suitable optical anisotropy is required. A product (Δn×d) of the optical anisotropy (Δn) of the composition and a cell gap (d) in the device is designed so as to maximize the contrast ratio. A suitable value of the product depends on a type of the operating mode. The suitable value is in the range of about 0.30 micrometer to about 0.40 micrometer in a device having the VA mode, and is in the range of about 0.20 micrometer to about 0.30 micrometer in a device having the IPS mode or the FFS mode. In the case, a composition having the large optical anisotropy is preferred for a device having a small cell gap. A large dielectric anisotropy in the composition contributes to a low threshold voltage, a small electric power consumption and a large contrast ratio in the device. Accordingly, the large dielectric anisotropy is preferred. Large specific resistance in the composition contributes to a large voltage holding ratio and the large contrast ratio in the device. Accordingly, a composition having the large specific resistance in an initial stage is preferred. The composition having the large specific resistance after the device has been used for a long period of time is preferred. Stability of the composition to ultraviolet light and heat relates to a service life of the device. In the case where the stability is high, the device has a long service life. Such characteristics are preferred for an AM device used in a liquid crystal monitor, a liquid crystal television and so forth.

Vertical alignment of liquid crystal molecules is achieved by a specific polyimide alignment film in a general-purpose liquid crystal display device. In a liquid crystal display device having a polymer sustained alignment (PSA) mode, the alignment film is combined with a polymer. First, a composition to which a small amount of a polymerizable compound is added is injected into the device. Then, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

A composition having positive dielectric anisotropy is used in an AM device having the TN mode. A composition having negative dielectric anisotropy is used in an AM device having the VA mode. A composition having the positive or negative dielectric anisotropy is used in an AM device having the IPS mode or the FFS mode. A composition having the positive or negative dielectric anisotropy is used in an AM device having the polymer sustained alignment (PSA) mode. The liquid crystal composition containing a quencher related to the invention is disclosed in Patent literature No. 1 described below.

CITATION LIST

Patent Literature

Patent literature No. 1: JP 2014-025025 A

SUMMARY OF INVENTION

Technical Problem

One of objectives of the invention is to provide a liquid crystal composition satisfying at least one of characteristics such as high maximum temperature of a nematic phase, low minimum temperature of the nematic phase, small viscosity, suitable optical anisotropy, large negative dielectric anisotropy, large specific resistance, high stability to ultraviolet light and high stability to heat. Another objective is to provide the liquid crystal composition having a suitable balance regarding at least two of the characteristics. Another objective is to provide a liquid crystal display device including such a composition. Another objective is to provide an AM device having characteristics such as a short response time, a large voltage holding ratio, a low threshold voltage, a large contrast ratio and a long service life.

Solution to Problem

The invention concerns a liquid crystal composition that contains a compound represented by formula (1) as a first additive, and has a nematic phase and negative dielectric anisotropy, and a liquid crystal display device including the composition.

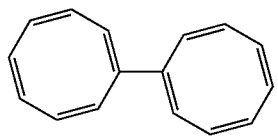

(1)

Advantageous Effects of Invention

One of advantages of the invention is to provide a liquid crystal composition satisfying at least one of characteristics such as high maximum temperature of a nematic phase, low minimum temperature of the nematic phase, small viscosity, suitable optical anisotropy, large negative dielectric anisotropy, large specific resistance, high stability to ultraviolet light and high stability to heat. Another advantage is to provide the liquid crystal composition having a suitable balance regarding at least two of the characteristics. Another advantage is to provide a liquid crystal display device including such a composition. Another advantage is to provide an AM device having characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but being mixed with the composition for the purpose of adjusting characteristics such as a temperature range of the nematic phase, viscosity and dielectric anisotropy. The compound has a six-membered ring such as 1,4-cyclohexylene and 1,4-phenylene, and has rod-like molecular structure. "Polymerizable compound" includes a compound to be added to the composition for the purpose of forming a polymer in the composition. A liquid crystal compound having alkenyl is not polymerizable in the above meaning.

The liquid crystal composition is prepared by mixing a plurality of liquid crystal compounds. An additive such as an optically active compound, an antioxidant, an ultraviolet light absorber, a dye, an antifoaming agent, the polymerizable compound, a polymerization initiator, a polymerization inhibitor and a polar compound is added when necessary. A proportion of the liquid crystal compound is expressed in terms of weight percent (% by weight) based on the weight of the liquid crystal composition containing no additive, even after the additive has been added. A proportion of the additive is expressed in terms of weight percent (% by weight) based on the weight of the liquid crystal composition containing no additive. More specifically, the proportion of the liquid crystal compound and the additive is calculated based on the total weight of the liquid crystal compound. Weight parts per million (ppm) may be occasionally used. A proportion of the polymerization initiator and the polymerization inhibitor is exceptionally expressed based on the weight of the polymerizable compound.

"Maximum temperature of the nematic phase" may be occasionally abbreviated as "maximum temperature." "Minimum temperature of the nematic phase" may be occasionally abbreviated as "minimum temperature." An expression "having large specific resistance" means that the composition has large specific resistance in an initial stage, and the composition has the large specific resistance even after the device has been used for a long period of time. An expression "having a large voltage holding ratio" means that the device has a large voltage holding ratio at room temperature and also at a temperature close to the maximum temperature in the initial stage, and the device has the large voltage holding ratio at room temperature and also at a temperature close to the maximum temperature even after the device has been used for the long period of time. The characteristics of the composition and the device may be occasionally examined by an aging test. An expression "increase the dielectric anisotropy" means that a value of dielectric anisotropy positively increases in a liquid crystal composition having positive dielectric anisotropy, and the value of dielectric anisotropy negatively increases in a liquid crystal composition having negative dielectric anisotropy.

An expression "at least one piece of —$CH_2$— may be replaced by —O—" is used herein. In the case, —$CH_2$—$CH_2$—$CH_2$— may be converted into —O—$CH_2$—O— by replacing pieces of —$CH_2$— that are not adjacent to each other by —O—. However, pieces of —$CH_2$— that are adjacent to each other never be replaced by —O—. The reason is that —O—O—CH$_2$-(peroxide) is formed in the replacement. More specifically, the above expression means both "one piece of —CH$_2$— may be replaced by —O—" and "at least two pieces of —CH$_2$— that are not adjacent to each other may be replaced by —O—." A same rule applies to replacement to —O—, and also to replacement to a divalent group such as —CH=CH— or —COO—.

A symbol of terminal group R$^1$ is used for a plurality of compounds in chemical formulas of component compounds. In the compounds, two of groups represented by any two pieces of R$^1$ may be identical or different. In one case, for example, R$^1$ of compound (2-1) is ethyl and R$^1$ of compound (2-2) is ethyl. In another case, R$^1$ of compound (2-1) is ethyl and R$^1$ of compound (2-2) is propyl. A same rule applies also to a symbol such as any other terminal groups. In formula (2), when a subscript 'a' is 2, two of rings A exist. In the compound, two of rings represented by two of rings A may be identical or different. A same rule applies also to any two of rings A when the subscript 'a' is larger than 2. A same rule applies also to symbols such as Z$^1$ and ring D. A same rule applies also to such a case where two pieces of -Sp$^2$-P$^5$ exist in compound (4-27).

Symbols such as A, B, C and D surrounded by a hexagonal shape correspond to rings such as ring A, ring B, ring C and ring D, respectively, and represent rings such as a six-membered ring and a condensed ring. In compound (4), an oblique line crossing the hexagonal shape represents that arbitrary hydrogen on the ring can be replaced by a group such as -Sp$^1$-P$^1$. A subscript such as 'e' represents the number of groups replaced. When the subscript 'e' is 0, no such replacement exists. When 'e' is 2 or more, a plurality of pieces of -Sp$^1$-P$^1$ exist on ring F. The plurality of groups represented by -Sp$^1$-P$^1$ may be identical or different. In an expression "ring A and ring B are independently X, Y or Z," the subject includes a plurality of subjects, and therefore "independently" is used. When the subject is "ring A," the subject includes a single subject, and therefore "independently" is not used.

Then, 2-fluoro-1,4-phenylene means two divalent groups described below. In a chemical formula thereof, fluorine may be leftward (L) or rightward (R). A same rule applies also to an asymmetrical divalent group formed by removing two hydrogen from a ring, such as tetrahydropyran-2,5-diyl. A same rule applies also to a divalent bonding group such as carbonyloxy (—COO or —OCO—).

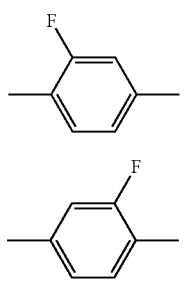

(L)

(R)

Alkyl of the liquid crystal compound is straight-chain alkyl or branched-chain alkyl, and includes no cyclic alkyl. Straight-chain alkyl is preferred to branched-chain alkyl. A same rule applies also to a terminal group such as alkoxy and alkenyl. With regard to a configuration of 1,4-cyclohex-ylene, trans is preferred to cis for increasing the maximum temperature.

The invention includes items described below.

Item 1. A liquid crystal composition that contains a compound represented by formula (1) as a first additive, and has a nematic phase and negative dielectric anisotropy:

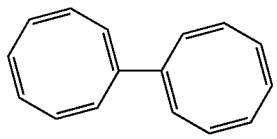

(1)

Item 2. The liquid crystal composition according to item 1, wherein a proportion of the first additive is in the range of 0.005% by weight to 2% by weight.

Item 3. The liquid crystal composition according to item 1 or 2, containing at least one compound selected from the group of compounds represented by formula (2) as a first component:

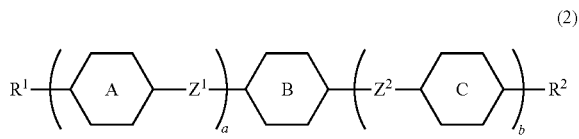

(2)

wherein, in formula (2), R$^1$ and R$^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen is replaced by fluorine or chlorine; ring A and ring C are independently 1,4-cyclohexylene, 1,4-cyclohexenylene, 1,4-phenylene, 1,4-phenylene in which at least one hydrogen is replaced by fluorine or chlorine, or tetrahydropyran-2,5-diyl; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; Z$^1$ and Z$^2$ are independently a single bond, ethylene, methyleneoxy or carbonyloxy; a is 1, 2 or 3, and b is 0 or 1; and a sum of a and b is 3 or less.

Item 4. The liquid crystal composition according to any one of items 1 to 3, containing at least one compound selected from the group of compounds represented by formula (2-1) to formula (2-22) as the first component:

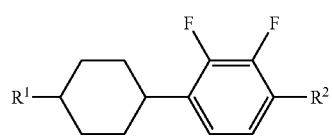

(2-1)

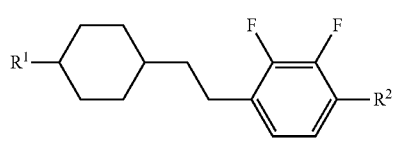

(2-2)

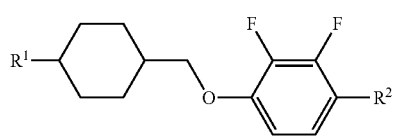

(2-3)

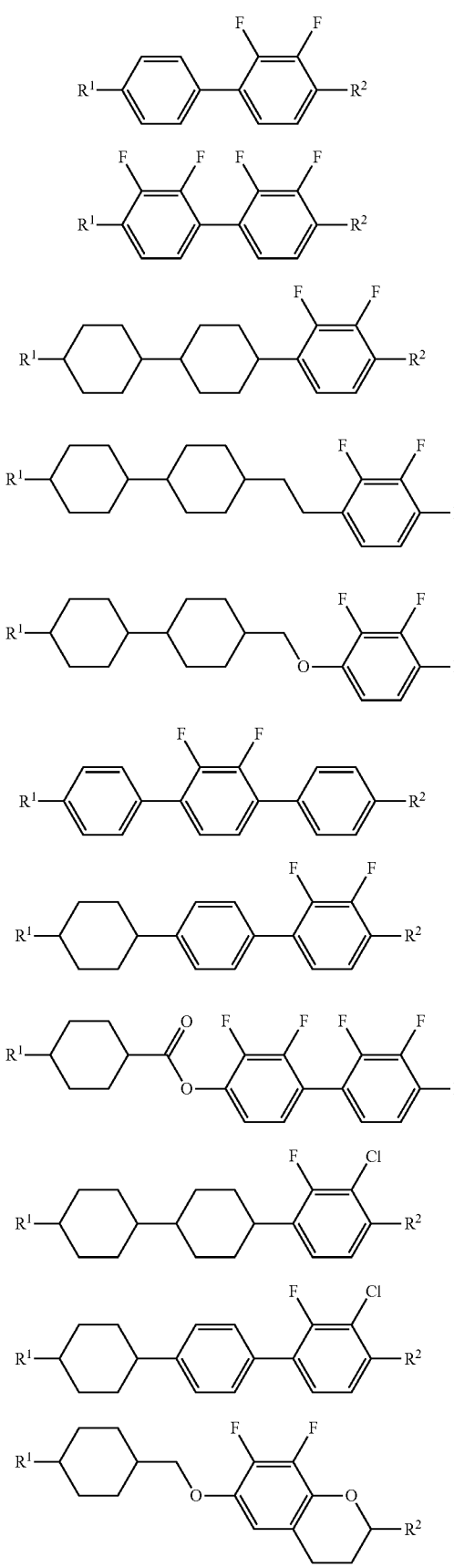
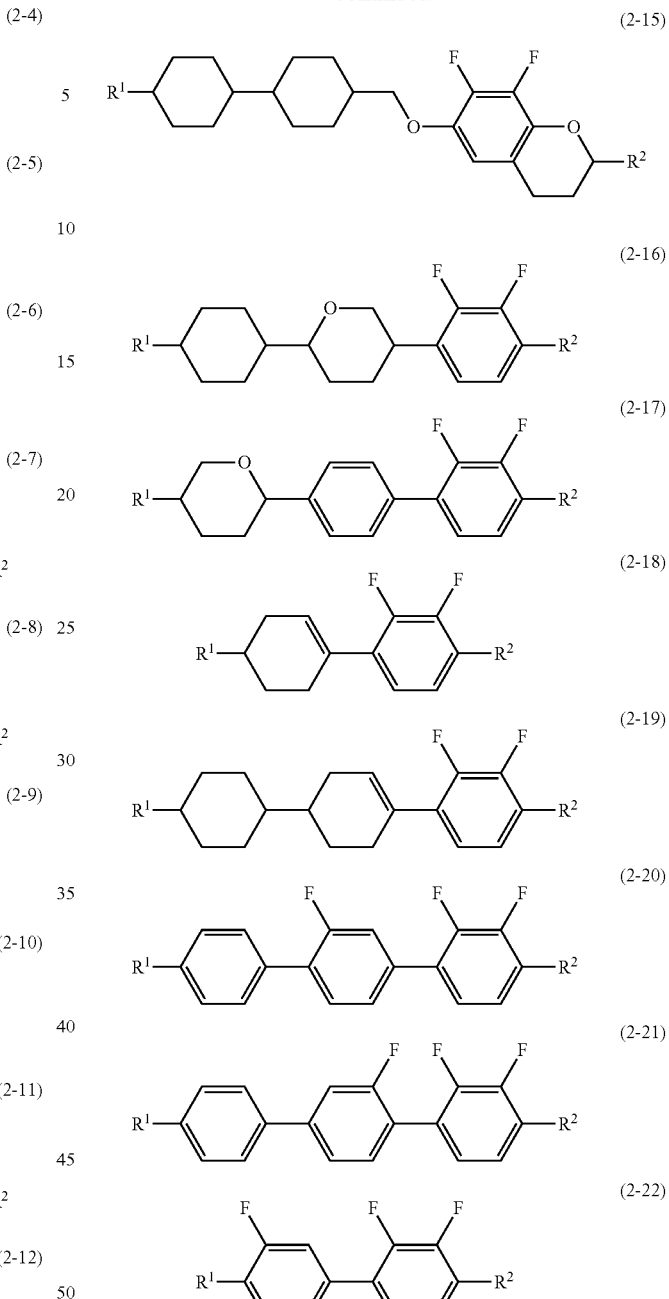

wherein, in formula (2-1) to formula (2-22), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen is replaced by fluorine or chlorine.

Item 5. The liquid crystal composition according to item 3 or 4, wherein a proportion of the first component is in the range of 10% by weight to 90% by weight.

Item 6. The liquid crystal composition according to any one of items 1 to 5, containing at least one compound selected from the group of compounds represented by formula (3) as a second component:

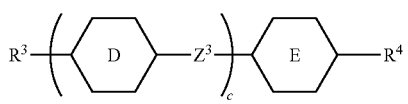
(3)

wherein, in formula (3), $R^3$ and $R^4$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine or chlorine; ring D and ring E are independently 1,4-cyclohexylene, 1,4-phenylene, 2-fluoro-1,4-phenylene or 2,5-difluoro-1,4-phenylene; $Z^3$ is a single bond, ethylene or carbonyloxy; and c is 1, 2 or 3.

Item 7. The liquid crystal composition according to any one of items 1 to 6, containing at least one compound selected from the group of compounds represented by formula (3-1) to formula (3-13) as the second component:

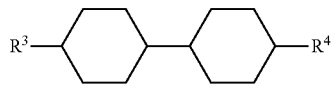
(3-1)

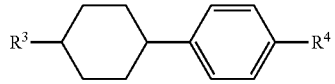
(3-2)

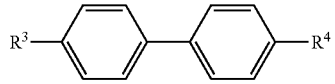
(3-3)

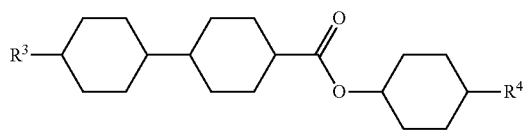
(3-4)

(3-5)

(3-6)

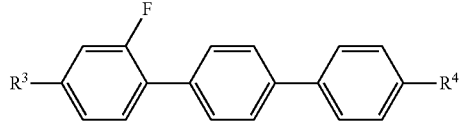
(3-7)

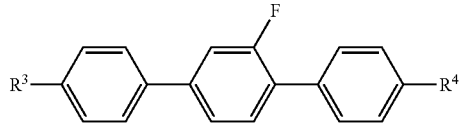
(3-8)

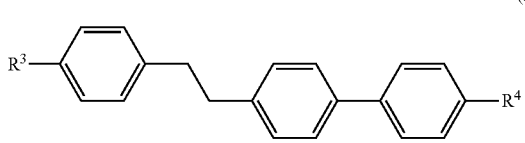
(3-9)

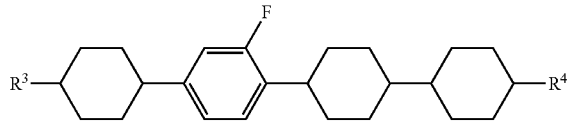
(3-10)

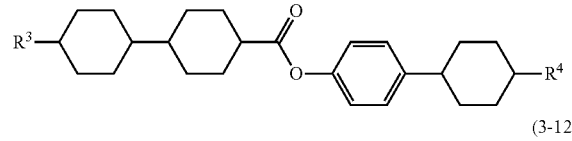
(3-11)

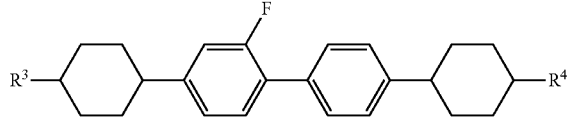
(3-12)

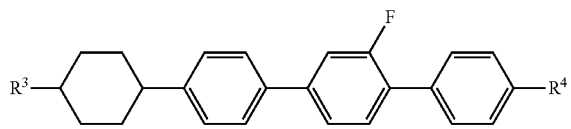
(3-13)

wherein, in formula (3-1) to formula (3-13), $R^3$ and $R^4$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine or chlorine.

Item 8. The liquid crystal composition according to item 6 or 7, wherein a proportion of the second component is in the range of 10% by weight to 90% by weight.

Item 9. The liquid crystal composition according to any one of items 1 to 8, containing at least one compound selected from the group of compounds represented by formula (4) as a second additive:

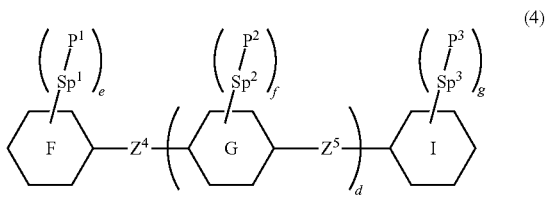
(4)

wherein, in formula (4), ring F and ring I are independently cyclohexyl, cyclohexenyl, phenyl, 1-naphthyl, 2-naphthyl, tetrahydropyran-2-yl or 1,3-dioxane-2-yl, pyrimidine-2-yl or pyridine-2-yl, and in the rings, at least one hydrogen may be replaced by fluorine, chlorine, alkyl having 1 to 12 carbons, alkoxy having 1 to 12 carbons, or alkyl having 1 to 12 carbons in which one hydrogen is replaced by fluorine or chlorine; ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by fluorine, chlorine, alkyl having 1 to 12 carbons, alkoxy having 1 to 12 carbons, or alkyl having 1 to 12 carbons in which at least one hydrogen is replaced by fluorine or chlorine; $Z^4$ and $Z^5$ are independently a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replaced by —CH=CH—, —C($CH_3$)=CH—, —CH=C($CH_3$)— or —C($CH_3$)=C($CH_3$)—, and in these groups, at least one hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one piece of —$CH_2$— may be replaced by —O—, —COO—, —OCO— or —OCOO—, and at least one piece of —$CH_2$—$CH_2$— may be replaced by —CH=CH— or —C≡C—, and in these groups, at least one hydrogen may be replaced by fluorine or chlorine; d is 0, 1 or 2; e, f and g are independently 0, 1, 2, 3 or 4; and a sum of e, f and g is 1 or more.

Item 10. The liquid crystal composition according to item 9, wherein, in formula (4), $P^1$, $P^2$ and $P^3$ are independently a group selected from the group of polymerizable groups represented by formula (P-1) to formula (P-5):

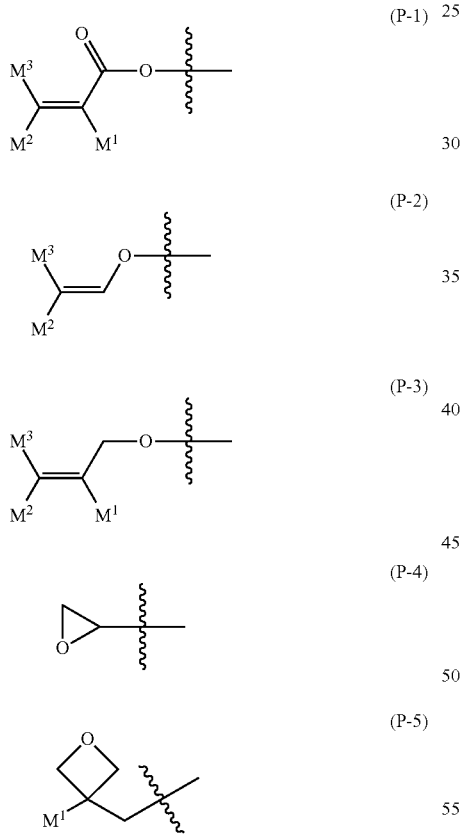

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one hydrogen is replaced by fluorine or chlorine.

Item 11. The liquid crystal composition according to any one of items 1 to 10, containing at least one compound selected from the group of polymerizable compounds represented by formula (4-1) to formula (4-27) as the second additive:

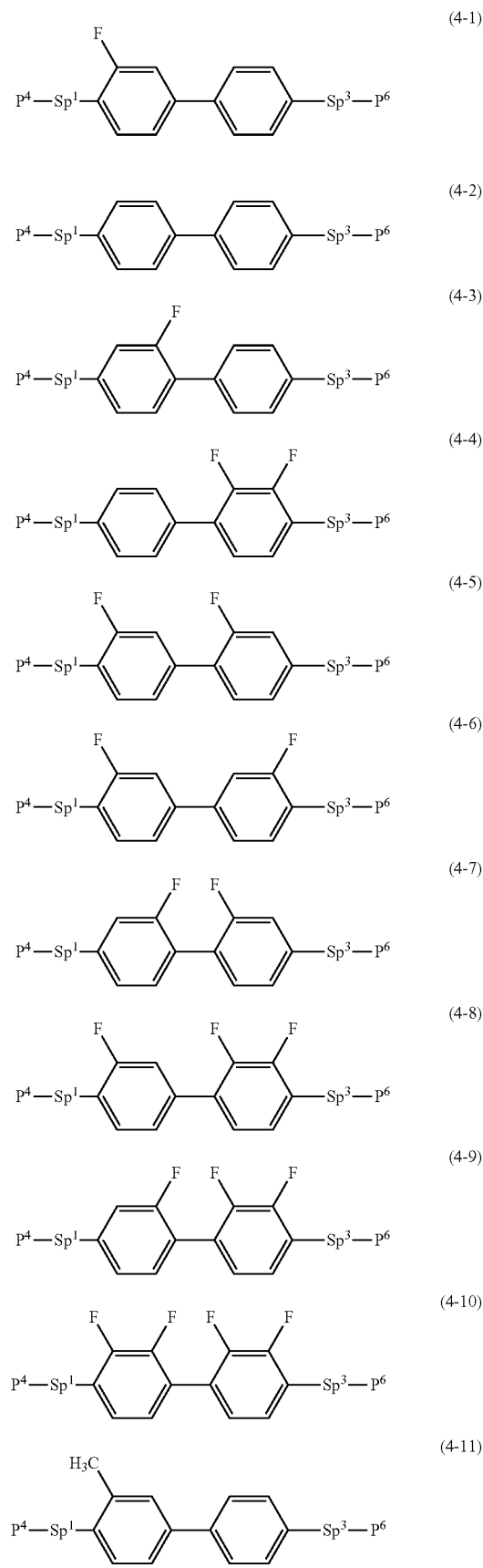

(4-12)
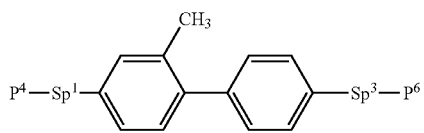
(4-13)
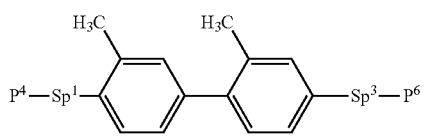
(4-14)
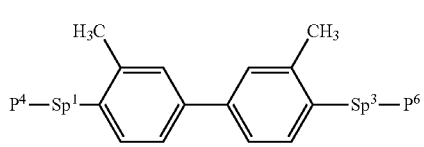
(4-15)
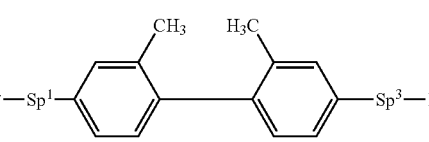
(4-16)
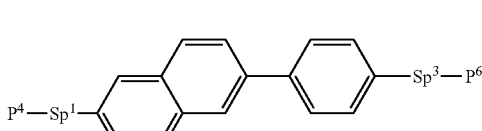
(4-17)
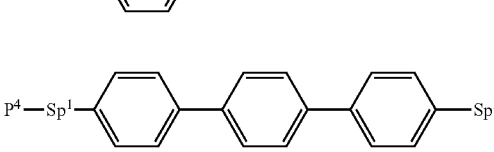
(4-18)
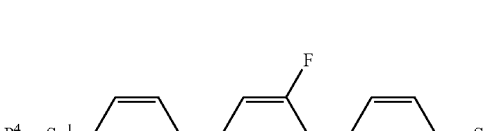
(4-19)
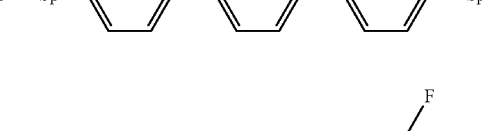
(4-20)
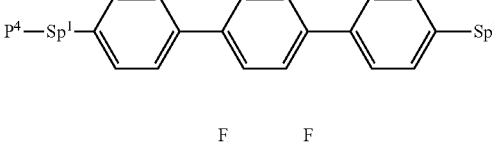
(4-21)
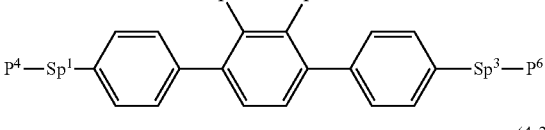
(4-22)
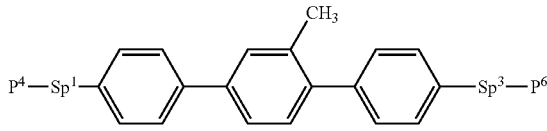
(4-23)
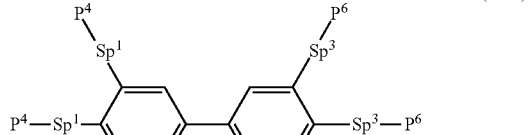
(4-24)
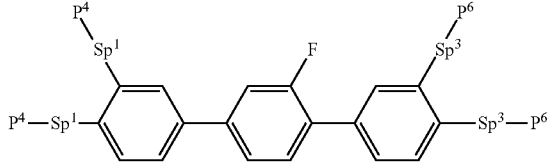
(4-25)
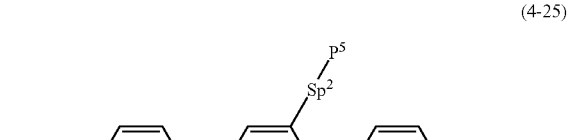
(4-26)
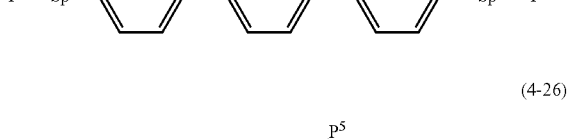
(4-27)
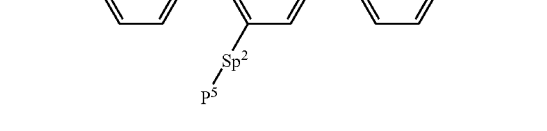
wherein, in formula (4-1) to formula (4-27), $P^4$, $P^5$ and $P^6$ are independently a polymerizable group selected from the group of groups represented by formula (P-1) to formula (P-3), in which $M^1$, $M^2$ and $M^3$ are independently hydrogen, fluorine, alkyl having 1 to 5 carbons, or alkyl having 1 to 5 carbons in which at least one hydrogen is replaced by fluorine or chlorine:

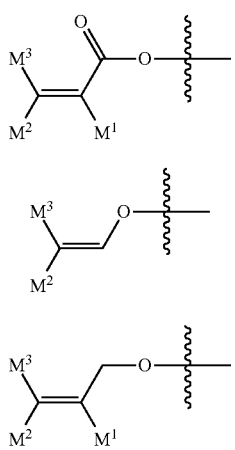

wherein, $Sp^1$, $Sp^2$ and $Sp^3$ are independently a single bond or alkylene having 1 to 10 carbons, and in the alkylene, at least one piece of —$CH_2$— may be replaced by —O—, —OCO—, —OCO— or —OCOO—, and at least one piece of —$CH_2$—$CH_2$— may be replaced by —CH=CH— or —C≡C—, and in these groups, at least one hydrogen may be replaced by fluorine or chlorine.

Item 12. The liquid crystal composition according to any one of items 9 to 11, wherein a proportion of the second additive is in the range of 0.03% by weight to 10% by weight.

Item 13. A liquid crystal display device including the liquid crystal composition according to any one of items 1 to 12.

Item 14. The liquid crystal display device according to item 13, wherein an operating mode in the liquid crystal display device includes an IPS mode, a VA mode, an FFS mode or an FPA mode, and a driving mode in the liquid crystal display device includes an active matrix mode.

Item 15. A polymer sustained alignment mode liquid crystal display device, wherein the liquid crystal display device includes the liquid crystal composition according to any one of items 9 to 12, and a polymerizable compound in the liquid crystal composition is polymerized.

Item 16. Use of the liquid crystal composition according to any one of items 1 to 12 in a liquid crystal display device.

Item 17. Use of the liquid crystal composition according to any one of items 9 to 12 in a polymer sustained alignment mode liquid crystal display device.

The invention further includes the following items: (a) the composition, further containing one, two or at least three of compounds selected from the group of additives such as an optically active compound, an antioxidant, an ultraviolet light absorber, a dye, an antifoaming agent, a polymerizable compound, a polymerization initiator and a polymerization inhibitor; (b) an AM device including the composition; (c) the composition further containing a polymerizable compound, and a polymer sustained alignment (PSA) mode AM device including the composition; (d) a polymer sustained alignment (PSA) mode AM device including the composition in which the polymerizable compound in the composition is polymerized; (e) a device including the composition, and having a PC, TN, STN, ECB, OCB, IPS, VA, FFS or FPA mode; (f) a transmissive device including the composition; (g) use of the composition as the composition having the nematic phase; and (h) use as an optically active composition by adding the optically active compound to the composition.

The composition of the invention will be described in the following order. First, a constitution of the composition will be described. Second, main characteristics of the component compounds and main effects of the compounds on the composition will be described. Third, a combination of components in the composition, a preferred proportion of the components and the basis thereof will be described. Fourth, a preferred embodiment of the component compounds will be described. Fifth, a preferred component compounds will be described. Sixth, an additive that may be added to the composition will be described. Seventh, methods for synthesizing the component compounds will be described. Last, an application of the composition will be described.

First, the constitution of the composition will be described. The composition contains a plurality of liquid crystal compounds. The composition may contain an additive. The additive is the optically active compound, the antioxidant, the ultraviolet light absorber, the dye, the antifoaming agent, the polymerizable compound, the polymerization initiator, the polymerization inhibitor, the polar compound or the like. The composition is classified into composition A and composition B. Composition A may further contain any other liquid crystal compound, an additive or the like in addition to the liquid crystal compound selected from compound (2) and compound (3). "Any other liquid crystal compound" means a liquid crystal compound different from compound (2) and compound (3). Such a compound is mixed with the composition for the purpose of further adjusting the characteristics.

Composition B consists essentially of the liquid crystal compound selected from compound (2) and compound (3). An expression "essentially" means that the composition may contain the additive, but contains no any other liquid crystal compound. Composition B has a smaller number of components than composition A has. Composition B is preferred to composition A in view of cost reduction. Composition A is preferred to composition B in view of ability of further adjusting the characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium" and a symbol S stands for "small" or "low." The symbols L, M and S represent a classification based on a qualitative comparison among the component compounds, and 0 (zero) means that a value is very small.

TABLE 2

| Characteristics of Compounds | | |
|---|---|---|
| Characteristics | Compound (2) | Compound (3) |
| Maximum temperature | S to L | S to L |
| Viscosity | M to L | S to M |
| Optical anisotropy | M to L | S to L |
| Dielectric anisotropy | M to L[1] | 0 |
| Specific resistance | L | L |

[1]Value of dielectric anisotropy is negative, and the symbol stands for magnitude of an absolute value.

The main effects of the component compounds are as described below. Compound (1) serves as a quencher, and contributes to the high stability to heat or ultraviolet light. Compound (1) is very small in adding amount, and therefore, in many cases, does not affect the characteristics such as the maximum temperature, the optical anisotropy and the dielectric anisotropy. Compound (2) increases the dielectric anisotropy and decreases the minimum temperature. Compound (3) decreases the viscosity or increases the maximum temperature. Compound (4) is polymerizable, and therefore gives a polymer by polymerization. The polymer stabilizes the alignment of the liquid crystal molecules, and therefore shortens a response time of the device and improves image persistence.

The quencher is a substance that returns a molecule from an excited state to a ground state. The molecule absorbs light to be excited. The molecule emits light when returned from the exited state to the ground state. A substance that receives energy from the excited molecule is referred to as the quencher. The quencher absorbs ultraviolet light, but the ability is small in comparison with the ultraviolet light absorber. A difference between the quencher and the ultraviolet light absorber will be described below. The ultraviolet light absorber is a compound that absorbs ultraviolet light preferentially in comparison with a substance desired to be protected from ultraviolet light, and converts the light energy into heat energy. On the other hand, the quencher is a compound that receives light energy absorbed by the substance desired to be protected, and converts the light energy into heat energy.

The quencher may occasionally have a problem of volatility thereof. If the quencher has high volatility, the quencher may volatilize in a process of injecting the liquid crystal composition to which the quencher is added to the device, thus causing inconsistency between an adding amount and an effect thereof. Accordingly, the volatility of the quencher is preferably as low as possible. Compound (1) is the useful quencher from such a viewpoint.

Third, the combination of components in the composition, a preferred proportion of the components and the basis thereof will be described. Preferred combinations of components in the composition include a combination of compound (1) and compound (2), a combination of compound (1) and compound (3), a combination of compound (1), compound (2) and compound (3), a combination of compound (1), compound (2) and compound (4), a combination of compound (1), compound (3) and compound (4) or a combination of compound (1), compound (2), compound (3) and compound (4). Further preferred combinations thereof include a combination of compound (1), compound (2) and compound (3) or a combination of compound (1), compound (2), compound (3) and compound (4).

A preferred proportion of compound (1) is about 0.005% by weight or more for increasing the stability to heat or ultraviolet light, and about 2% by weight or less for decreasing the minimum temperature. A further preferred proportion is in the range of about 0.01% by weight to about 1% by weight. A particularly preferred proportion is in the range of about 0.03% by weight to about 0.5% by weight.

A preferred proportion of compound (2) is about 10% by weight or more for increasing the dielectric anisotropy, and about 90% by weight or less for decreasing the minimum temperature. A further preferred proportion is in the range of about 20% by weight to about 80% by weight. A particularly preferred proportion is in the range of about 30% by weight to about 7 by weight.

A preferred proportion of compound (3) is about 10% by weight or more for increasing the maximum temperature or for decreasing the viscosity, and about 90% by weight or less for increasing the dielectric anisotropy. A further preferred proportion is in the range of about 20% by weight to about 80% by weight. A particularly preferred proportion is in the range of about 30% by weight to about 70% by weight.

Compound (4) is added to the composition for the purpose of adapting the composition to the polymer sustained alignment mode device. A preferred proportion of compound (4) is about 0.03% by weight for aligning the liquid crystal molecules, and about 10% by weight or less for preventing poor display of the device. A further preferred proportion is in the range of about 0.1% by weight to about 2% by weight. A particularly preferred proportion is in the range of about 0.2% by weight to about 1.0% by weight.

Fourth, the preferred embodiment of the component compounds will be described. In formula (2) and formula (3), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen is replaced by fluorine or chlorine. Preferred $R^1$ or $R^2$ is alkyl having 1 to 12 carbons for increasing the stability, and alkoxy having 1 to 12 carbons for increasing the dielectric anisotropy. $R^3$ and $R^4$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine or chlorine. Preferred $R^3$ or $R^4$ is alkenyl having 2 to 12 carbons for decreasing the viscosity, and alkyl having 1 to 12 carbons for increasing the stability.

Preferred alkyl is methyl, ethyl, propyl, butyl, pentyl, hexyl, heptyl or octyl. Further preferred alkyl is methyl, ethyl, propyl, butyl or pentyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH=CH— in the alkenyl depends on a position of a double bond. Trans is preferred in alkenyl such as 1-propenyl, 1-butenyl, 1-pentenyl, 1-hexenyl, 3-pentenyl and 3-hexenyl for decreasing the viscosity, for instance. Cis is preferred in alkenyl such as 2-butenyl, 2-pentenyl and 2-hexenyl.

Preferred alkenyloxy is vinyloxy, allyloxy, 3-butenyloxy, 3-pentenyloxy or 4-pentenyloxy. Further preferred alkenyloxy is allyloxy or 3-butenyloxy for decreasing the viscosity.

Preferred examples of alkyl in which at least one of hydrogen is replaced by fluorine or chlorine include fluoromethyl, 2-fluoroethyl, 3-fluoropropyl, 4-fluorobutyl, 5-fluoropentyl, 6-fluorohexyl, 7-fluoroheptyl or 8-fluorooctyl. Further preferred examples include 2-fluoroethyl, 3-fluoropropyl, 4-fluorobutyl or 5-fluoropentyl for increasing the dielectric anisotropy.

Preferred examples of alkenyl in which at least one of hydrogen is replaced by fluorine or chlorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Ring A and ring C are independently 1,4-cyclohexylene, 1,4-cyclohexenylene, 1,4-phenylene, 1,4-phenylene in which at least one hydrogen is replaced by fluorine or chlorine, or tetrahydropyran-2,5-diyl. Preferred examples of "1,4-phenylene in which at least one hydrogen is replaced by fluorine or chlorine" include 2-fluoro-1,4-phenylene, 2,3-difluoro-1,4-phenylene or 2-chloro-3-fluoro-1,4-phenylene. Preferred ring A or ring C is 1,4-cyclohexylene for decreasing the viscosity, tetrahydropyran-2,5-diyl for increasing the dielectric anisotropy, and 1,4-phenylene for increasing the optical anisotropy. Tetrahydropyran-2,5-diyl includes:

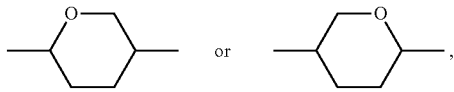

preferably

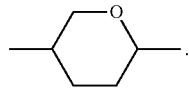

Ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring B is 2,3-difluoro-1,4-phenylene for decreasing the viscosity, 2-chloro-3-fluoro-1,4-phenylene for decreasing the optical anisotropy, and 7,8-difluorochroman-2,6-diyl for increasing the dielectric anisotropy.

Ring D and ring E are independently 1,4-cyclohexylene, 1,4-phenylene, 2-fluoro-1,4-phenylene or 2,5-difluoro-1,4-phenylene. Preferred ring D or ring E is 1,4-cyclohexylene for decreasing the viscosity or for increasing the maximum temperature, and 1,4-phenylene for decreasing the minimum temperature.

$Z^1$ and $Z^2$ are independently a single bond, ethylene, methyleneoxy or carbonyloxy. Preferred $Z^1$ or $Z^2$ is a single bond for decreasing the viscosity, ethylene for decreasing the minimum temperature, and methyleneoxy for increasing the dielectric anisotropy. $Z^3$ is a single bond, ethylene or carbonyloxy. Preferred $Z^3$ is a single bond for decreasing the viscosity.

Then, a is 1, 2, or 3. Preferred a is 1 for decreasing the viscosity, and is 2 or 3 for increasing the maximum temperature. Then, b is 0 or 1. Preferred b is 0 for decreasing the viscosity, and 1 for decreasing the minimum temperature. Then, c is 1, 2, or 3. Preferred c is 1 for decreasing the viscosity, and is 2 or 3 for increasing the maximum temperature.

In formula (4), $P^1$, $P^2$ and $P^3$ are independently a polymerizable group. Preferred $P^1$, $P^2$ or $P^3$ is a polymerizable group selected from the group of groups represented by formula (P-1) to formula (P-5). Further preferred $P^1$, $P^2$ or $P^3$ is group (P-1) or group (P-2). Particularly preferred group (P-1) is —OCO—CH=CH$_2$ or —OCO—C(CH$_3$)=CH$_2$. A wavy line in group (P-1) to group (P-5) represents a site to be bonded.

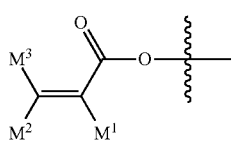

(P-1)

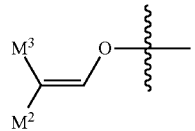

(P-2)

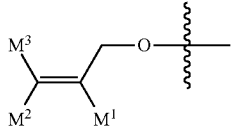

(P-3)

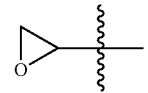

(P-4)

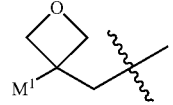

(P-5)

In group (P-1) to group (P-5), $M^1$, $M^2$ and $M^3$ are independently hydrogen, fluorine, alkyl having 1 to 5 carbons, or alkyl having 1 to 5 carbons in which at least one hydrogen is replaced by fluorine or chlorine. Preferred $M^1$, $M^2$ or $M^3$ is hydrogen or methyl for increasing reactivity. Further preferred $M^1$ is methyl, and further preferred $M^2$ or $M^3$ is hydrogen.

In formula (4-1) to formula (4-27), $P^4$, $P^5$ and $P^6$ are independently a group represented by formula (P-1) to formula (P-3). Preferred $P^4$, $P^5$ or $P^6$ is group (P-1) or group (P-2). Further preferred group (P-1) is —OCO—CH=CH$_2$ or —OCO—C(CH$_3$)=CH$_2$. A wavy line from group (P-1) to group (P-3) represents a site to be bonded.

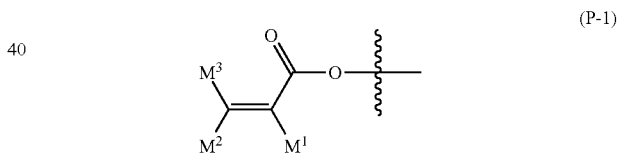

(P-1)

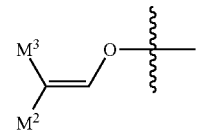

(P-2)

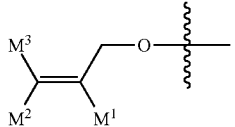

(P-3)

In formula (4), $Sp^1$, $Sp^2$ and $Sp^3$ are independently a single bond or alkylene having 1 to 10 carbons, and in the alkylene, at least one piece of —CH$_2$— may be replaced by —O—, —COO—, —OCO—, or —OCOO—, and at least one piece of —CH$_2$—CH$_2$— may be replaced by —CH=CH— or —C≡C—, and in these groups, at least one hydrogen may be replaced by fluorine or chlorine. Preferred $Sp^1$, $Sp^2$ or $Sp^3$ is a single bond, —CH$_2$CH$_2$—, —CH$_2$O—, —OCH$_2$—, —OCO—, —OCO—, —CO—CH=CH— or —CH=CH—CO—. Further preferred $Sp^1$, $Sp^2$ or $Sp^3$ is a single bond.

Ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by fluorine or chlorine, alkyl having 1 to 12 carbons, alkoxy having 1 to 12 carbons, or alkyl having 1 to 12 carbons in which at least one hydrogen is replaced by fluorine or chlorine. Preferred ring F or ring I is phenyl. Ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by fluorine, chlorine, alkyl having 1 to 12 carbons, alkoxy having 1 to 12 carbons, or alkyl having 1 to 12 carbons in which at least one hydrogen may be replaced by fluorine or chlorine. Preferred ring G is 1,4-phenylene or 2-fluoro-1,4-phenylene.

$Z^4$ and $Z^5$ are independently a single bond or alkylene having 1 to 10 carbons, and in the alkylene, at least one piece of —$CH_2$— may be replaced by —O—, —CO—, —COO— or —OCO—, and at least one piece of —$CH_2$—$CH_2$— may be replaced by —CH=CH—, —C($CH_3$)=CH—, —CH=C($CH_3$)— or —C($CH_3$)=C($CH_3$)—, and in these groups, at least one hydrogen may be replaced by fluorine or chlorine. Preferred $Z^4$ or $Z^5$ is a single bond, —$CH_2CH_2$—, —$CH_2O$—, —$OCH_2$—, —COO— or —OCO—. Further preferred $Z^4$ or $Z^5$ is a single bond.

Then, d is 0, 1 or 2. Preferred d is 0 or 1. Then, e, f, and g are independently 0, 1, 2, 3 or 4, and a sum of e, f and g is 1 or more. Preferred e, for g is 1 or 2.

Fifth, the preferred component compounds will be described. Preferred compound (2) includes compound (2-1) to compound (2-22) described in item 4. In the compounds, at least one of the first components preferably includes compound (2-1), compound (2-3), compound (2-4), compound (2-6), compound (2-8) or compound (2-10). At least two of the first components preferably include a combination of compound (2-1) and compound (2-6), a combination of compound (2-1) and compound (2-10), a combination of compound (2-3) and compound (2-6), a combination of compound (2-3) and compound (2-10), a combination of compound (2-4) and compound (2-6) or a combination of compound (2-4) and compound (2-8).

Preferred compound (3) includes compound (3-1) to compound (3-13) described in item 7. In the compounds, at least one of the second components preferably include compound (3-1), compound (3-3), compound (3-5), compound (3-6), compound (3-8) or compound (3-9). At least two of the second components preferably include a combination of compound (3-1) and compound (3-3), a combination of compound (3-1) and compound (3-5) or a combination of compound (3-1) and compound (3-6).

Preferred compound (4) includes compound (4-1) to compound (4-27) described in item 11. In the compounds, at least one of the second additives preferably includes compound (4-1), compound (4-2), compound (4-24), compound (4-25), compound (4-26) or compound (4-27). At least two of the second additives preferably include a combination of compound (4-1) and compound (4-2), a combination of compound (4-1) and compound (4-18), a combination of compound (4-2) and compound (4-24), a combination of compound (4-2) and compound (4-25), a combination of compound (4-2) and compound (4-26), a combination of compound (4-25) and compound (4-26) or a combination of compound (4-18) and compound (4-24).

Sixth, the additive that may be added to the composition will be described. Such an additive includes the optically active compound, the antioxidant, the ultraviolet light absorber, the dye, the antifoaming agent, the polymerizable compound, the polymerization initiator, the polymerization inhibitor and the like. The optically active compound is added to the composition for the purpose of inducing a helical structure in the liquid crystal molecule to give a twist angle. Examples of such a compound include compound (5-1) to compound (5-5). A preferred proportion of the optically active compound is about 5% by weight or less. A further preferred proportion is in the range of about 0.01% by weight to about 2% by weight.

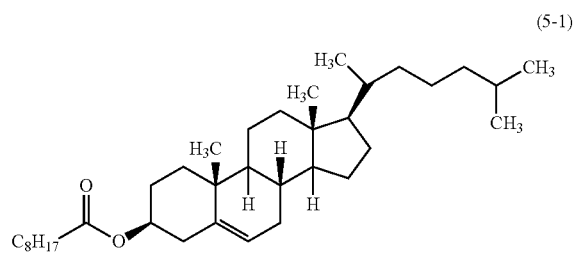

(5-1)

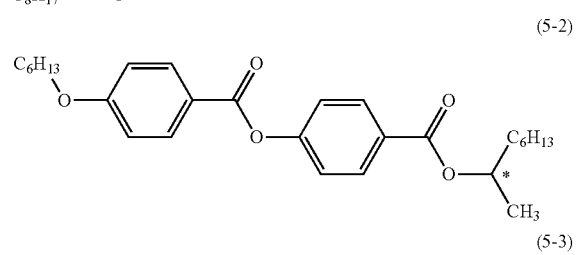

(5-2)

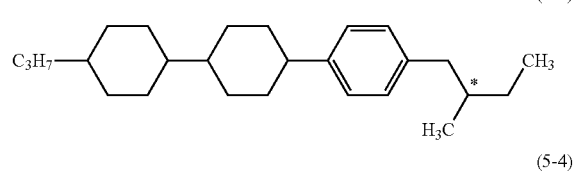

(5-3)

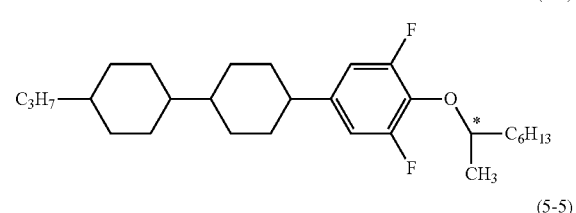

(5-4)

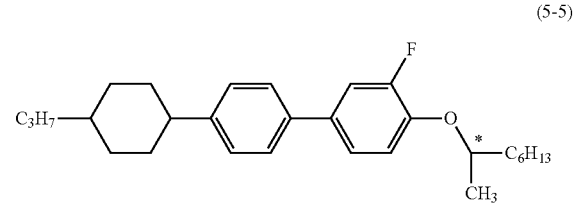

(5-5)

The antioxidant is added to the composition for preventing a decrease in the specific resistance caused by heating in air, or for maintaining a large voltage holding ratio at room temperature and also at the temperature close to the maximum temperature even after the device has been used for a long period of time. Preferred examples of the antioxidant include compound (6) where n is an integer from 1 to 9.

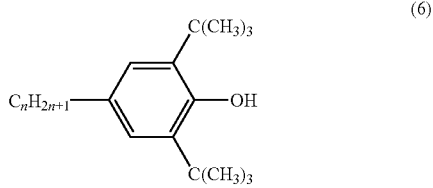

(6)

In compound (6), preferred n is 1, 3, 5, 7 or 9. Further preferred n is 7. Compound (6) where n is 7 is effective in maintaining a large voltage holding ratio at room temperature and also at the temperature close to the maximum temperature even after the device has been used for a long period of time because such compound (6) has a small volatility. A preferred proportion of the antioxidant is about 50 ppm or more for achieving an effect thereof, and about 600 ppm or less for avoiding a decrease in the maximum temperature or an increase in the minimum temperature. A further preferred proportion is in the range of about 100 ppm to about 300 ppm.

Compound (1) is useful as the quencher. The ultraviolet light absorber may be added to the composition together with the quencher. Preferred examples of the ultraviolet light absorbent include a benzophenone derivative, a benzoate derivative and a triazole derivative. The light stabilizer such as amine having steric hindrance is also preferred.

A dichroic dye such as an azo dye or an anthraquinone dye is added to the composition to be adapted for a device having a guest host (GH) mode. A preferred proportion of the dye is in the range of about 0.01% by weight to about 10% by weight. The antifoaming agent such as dimethyl silicone oil or methyl phenyl silicone oil is added to the composition for preventing foam formation. A preferred proportion of the antifoaming agent is about 1 ppm or more for achieving an effect thereof, and about 1,000 ppm or less for preventing a poor display. A further preferred proportion is in the range of about 1 ppm to about 500 ppm.

The polymerizable compound is used to be adapted for a polymer sustained alignment (PSA) mode device. Compound (4) is suitable for the purpose. Any other polymerizable compound that is different from compound (4) may be added to the composition together with compound (4). Preferred examples of the polymerizable compounds include acrylate, methacrylate, a vinyl compound, a vinyloxy compound, propenyl ether, an epoxy compound (oxirane, oxetane) and vinyl ketone compound. Further preferred examples include an acrylate derivative or a methacrylate derivative. A preferred proportion of compound (4) is 10% by weight or more based on the total weight of the polymerizable compound. A further preferred proportion is 50% by weight or more. A particularly preferred proportion is 80% by weight or more. A most preferred proportion is 100% by weight.

The polymerizable compound such as compound (4) is polymerized by irradiation with ultraviolet light. The polymerizable compound may be polymerized in the presence of a suitable initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred proportion of the photopolymerization initiator is in the range of about 0.1% by weight to about 5% by weight based on the total weight of the polymerizable compound. A further preferred proportion is in the range of about 1% by weight to about 3% by weight based thereon.

Upon storing the polymerizable compound such as compound (4), the polymerization inhibitor may be added thereto for preventing polymerization. The polymerizable compound is ordinarily added to the composition without removing the polymerization inhibitor. Specific examples of the polymerization inhibitor include a hydroquinone derivative such as hydroquinone and methylhydroquinone, 4-t-butylcatechol, 4-methoxyphenol and phenothiazine.

Seventh, methods for synthesizing the component compounds will be described. The compounds can be prepared according to known methods. Examples of the synthetic methods are described. Compound (1) is prepared by the method described in Journal of the American Chemical Society (1953), 75, 3210. Compound (2-1) is prepared by the method described in JP 2000-053602 A. Compound (3-1) is prepared by the method described in JP S59-176221 A. Compound (4-18) is prepared by the method described in JP H7-101900 A. The antioxidant is commercially available. A compound represented by formula (6) where n is 1 is available from Sigma-Aldrich Corporation. Compound (6) where n is 7 or the like are prepared according to the method described in U.S. Pat. No. 3,660,505 B.

Any compounds whose synthetic methods are not described can be prepared according to methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition mainly has a minimum temperature of about −10° C. or lower, a maximum temperature of about 70° C. or higher, and optical anisotropy in the range of about 0.07 to about 0.20. The composition having optical anisotropy in the range of about 0.08 to about 0.25 may be prepared by controlling the ratio of the component compounds or by mixing any other liquid crystal compound. The composition having the optical anisotropy in the range of about 0.10 to about 0.30 may be prepared by trial and error. A device including the composition has the large voltage holding ratio. The composition is suitable for use in the AM device. The composition is particularly suitable for use in a transmissive AM device. The composition can be used as the composition having the nematic phase, and as the optically active composition by adding the optically active compound.

The composition can be used in the AM device. The composition can also be used in a PM device. The composition can also be used in an AM device and a PM device each having a mode such as the PC mode, the TN mode, the STN mode, the ECB mode, the OCB mode, the IPS mode, the FFS mode, the VA mode and the FPA mode. Use for the AM device having the TN mode, the OCB mode, the IPS mode or the FFS mode is particularly preferred. In the AM device having the IPS mode or the FFS mode, alignment of liquid crystal molecules when no voltage is applied may be parallel or vertical to a glass substrate. The device may be of a reflective type, a transmissive type or a transflective type. Use for the transmissive device is preferred. The composition can also be used in an amorphous silicon-TFT device or a polycrystal silicon-TFT device. The composition can also be used in a nematic curvilinear aligned phase (NCAP) device prepared by microencapsulating the composition, or for a polymer dispersed (PD) device in which a three-dimensional network-polymer is formed in the composition.

EXAMPLES

The invention will be described in greater detail by way of Examples. The invention is not limited by the Examples. The invention includes a mixture of a composition in Example 1 and a composition in Example 2. The invention also includes a mixture prepared by mixing at least two of compositions in Examples. A compound prepared was identified by methods such as an NMR analysis. Characteristics of the compound, the composition and a device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-14B Gas Chromatograph made by Shimadzu Corporation was used. A carrier gas was helium (2 mL/min). A sample vaporizing chamber and a detector (FID) were set to 280° C. and 300° C., respectively. A capillary column DB-1 (length 30 m, bore 0.32 mm, film thickness 0.25 dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample vaporizing chamber. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of preventing an overlap of peaks of the compounds.

A proportion of liquid crystal compounds contained in the composition may be calculated by a method as described below. A mixture of liquid crystal compounds is analyzed by gas chromatograph (FID). An area ratio of each peak in the gas chromatogram corresponds to the proportion of the liquid crystal compound. When the capillary columns described above were used, a correction coefficient of each of the liquid crystal compounds may be regarded as 1.

Accordingly, the proportion (% by weight) of the liquid crystal compounds can be calculated from the area ratio of each peak.

Sample for measurement: When characteristics of the composition and the device were measured, the composition was used as was. Upon measuring characteristics of a compound, a sample for measurement was prepared by mixing the compound (15% by weight) with a base liquid crystal (85% by weight). Values of characteristics of the compound were calculated, according to an extrapolation method, using values obtained by measurement: (Extrapolated value)={(measured value of a sample for measurement)−0.85×(measured value of a base liquid crystal)}/0.15. When a smectic phase (or crystals) precipitates at the ratio thereof at 25° C., a ratio of the compound to the base liquid crystal was changed step by step in the order of (10% by weight:90% by weight), (5% by weight:95% by weight) and (1% by weight:99% by weight). Values of maximum temperature, optical anisotropy, viscosity and dielectric anisotropy with regard to the compound were determined according to the extrapolation method.

A base liquid crystal described below was used. A proportion of the component compound was expressed in terms of weight percent (% by weight).

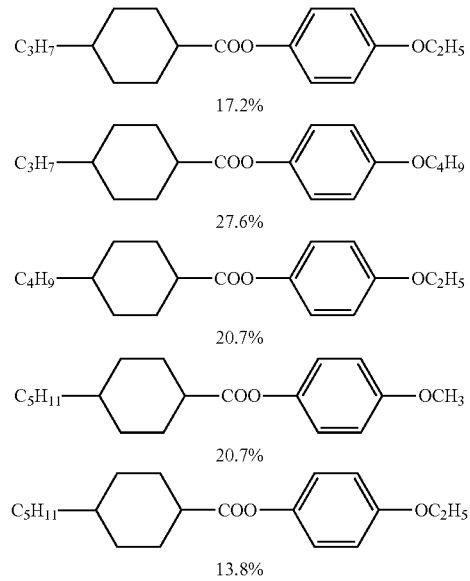

Measuring method: Physical properties were measured according to the methods described below. Most of the methods are described in the Standard of Japan Electronics and Information Technology Industries Association (hereinafter, abbreviated as JEITA) discussed and established in JEITA (JEITA ED-2521B). A modification of the methods was also used. No thin film transistor (TFT) was attached to a TN device used for measurement.

(1) Maximum temperature of a nematic phase (NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. A higher limit of the temperature range of the nematic phase may be occasionally abbreviated as "maximum temperature."

(2) Minimum temperature of a nematic phase (Tc; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained in the nematic phase at −20° C. and changed to crystals or a smectic phase at −30° C., Tc of the sample was expressed as Tc<−20° C. A lower limit of the temperature range of the nematic phase may be occasionally abbreviated as "minimum temperature."

(3) Viscosity (bulk viscosity; 11; measured at 20° C.; mPa·s): For measurement, an E type rotational viscometer by Tokyo Keiki Co., Ltd. was used.

(4) Viscosity (rotational viscosity; γ1; measured at 25° C.; mPa·s): Measurement was carried out according to the method described in M. Imai et al., Molecular Crystals and Liquid Crystals, Vol. 259, p. 37 (1995). A sample was put in a TN device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values according to calculating equation (8) on page 40 of the paper presented by M. Imai et al. Dielectric anisotropy required for the calculation was measured by a method described in section (6) described below.

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n//) was measured when the direction of polarized light was parallel to the direction of rubbing. A refractive index (n⊥) was measured when the direction of polarized light was perpendicular to the direction of rubbing. A value of the optical anisotropy (Δn) was calculated from an equation: Δn=n//−n⊥.

(6) Dielectric anisotropy (Δε; measured at 25° C.): A value of the dielectric anisotropy was calculated from an equation: Δε=ε//−ε⊥. A dielectric constant (ε//and ε⊥) was measured as described below.

1) Measurement of a dielectric constant (ε//): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε//) in a major axis direction of the liquid crystal molecules was measured.

2) Measurement of a dielectric constant (ε⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε⊥) in the minor axis direction of the liquid crystal molecules was measured.

(7) Threshold voltage (Vth; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 10% transmittance.

(8) Voltage holding ratio (VHR-9; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (60 microseconds at 1 V) was applied to the TN device and the device was charged. A decaying voltage was measured for 166.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage holding ratio (VHR-10; measured at 60° C.; %): A voltage holding ratio was measured according to a procedure identical to the procedure described above except that measurement was carried out at 60° C. in place of 25° C. The value thus obtained was expressed in terms of VHR-10.

(10) Voltage holding ratio (VHR-11; measured at 60° C.; %): Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with ultraviolet light of 5 mW/cm$^2$ for 167 minutes. A light source was a black light F40T10/BL (peak wavelength 369 nm) made by EYE GRAPHICS CO., LTD., and a distance between the device and the light source was 5 millimeters. In measurement of VHR-11, a decaying voltage was measured for 166.7 milliseconds. A composition having large VHR-11 has a large stability to ultraviolet light.

(11) Voltage holding ratio (VHR-12; measured at 60° C.; %): Stability to heat was evaluated by measuring a voltage holding ratio after a TN device into which a sample was injected was heated in a constant-temperature bath at 120° C. for 20 hours. In measurement of VHR-12, a decaying voltage was measured for 166.7 milliseconds. A composition having large VHR-12 has a large stability to heat.

(12) Response time (τ; measured at 25° C.; ms): For measurement, an LCD-5100 luminance meter made by Otsuka Electronics Co., Ltd. was used. A light source was a halogen lamp. A low-pass filter was set to 5 kHz. A sample was put in a normally black mode VA device in which a distance (cell gap) between two glass substrates was 4 micrometers and a rubbing direction was anti-parallel. The device was sealed with an ultraviolet-curable adhesive. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

(13) Specific resistance (p; measured at 25° C.; Ωcm): Into a vessel equipped with electrodes, 1.0 milliliter of a sample was injected. A direct current voltage (10 V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

Examples of the composition will be described below. The component compounds were represented by symbols based on the definition of the following Table 3. In Table 3, a configuration of 1,4-cyclohexylene is trans. Parenthesized numbers described after the symbols in Examples represent formulas to which the compounds belong. A symbol (-) means any other liquid crystal compound. A proportion (percentage) of the liquid crystal compound is a weight percent (% by weight) based on the weight of the liquid crystal composition containing no additives. Values of characteristic of the liquid crystal composition were summarized in a last part.

TABLE 3

Method for Description of Compounds using Symbols
R—(A$_1$)—Z$_1$— . . . —Z$_n$—(A$_n$)—R'

| 1) Left-terminal Group R— | Symbol |
|---|---|
| F—C$_n$H$_{2n}$— | Fn— |
| C$_n$H$_{2n+1}$— | n— |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| CH$_2$=CH—COO— | AC— |
| CH$_2$=C(CH$_3$)—COO— | MAC— |

| 2) Right-terminal Group —R' | Symbol |
|---|---|
| —C$_n$H$_{2n+1}$ | —n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —OCO—CH=CH$_2$ | —AC |
| —OCO—C(CH$_3$)=CH$_2$ | —MAC |

| 3) Bonding Group —Z$_n$— | Symbol |
|---|---|
| —C$_n$H$_{2n}$— | n |
| —COO— | E |
| —CH=CH— | V |
| —CH=CHO— | VO |
| —OCH=CH— | OV |

TABLE 3-continued

Method for Description of Compounds using Symbols
R—(A$_1$)—Z$_1$— . . . —Z$_n$—(A$_n$)—R'

| | |
|---|---|
| —CH$_2$O— | 1O |
| —OCH$_2$— | O1 |

| 4) Ring Structure —A$_n$— | Symbol |
|---|---|
| 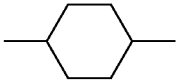 | H |
| 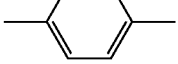 | B |
| 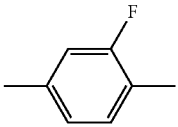 | B(F) |
| 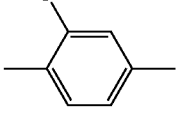 | B(2F) |
| 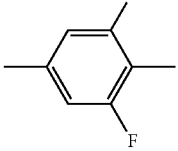 | B(F,F) |
| 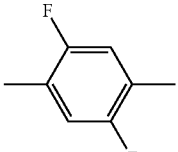 | B(2F,5F) |
| 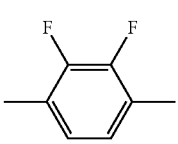 | B(2F,3F) |
| 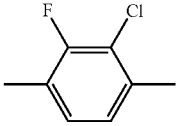 | B(2F,3Cl) |
| 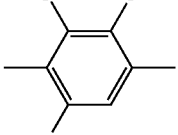 | B(2F,3F,6Me) |
| 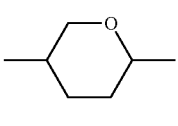 | dh |

TABLE 3-continued

Method for Description of Compounds using Symbols
R—(A₁)—Z₁— . . . —Zₙ—(Aₙ)—R'

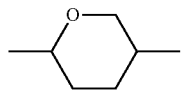  Dh

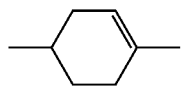  ch

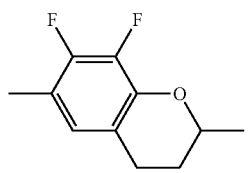  Cro(7F,8F)

5) Examples of Description

Example 1. 3—HH1OB(2F,3F)—O2

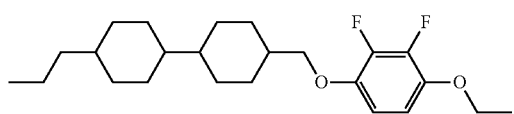 [SMILES: CCCC1CCC(C2CCC(COc3ccc(OCC)c(F)c3F)CC2)CC1]

Example 2. 3—HHB(2F,3F)—O2

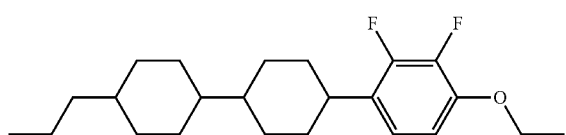 [SMILES: CCCC1CCC(C2CCC(c3ccc(OCC)c(F)c3F)CC2)CC1]

Example 3. V—HHB—1

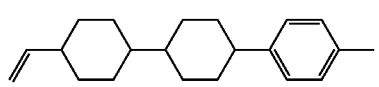

Example 4. 2—BB(F)B—3

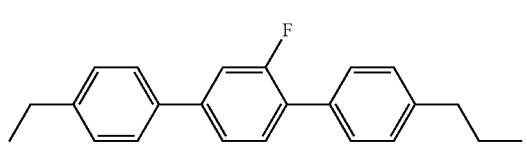

Example 1

| | | |
|---|---|---|
| 3-BB(2F,3F)-O2 | (2-4) | 13% |
| 2-HH1OB(2F,3F)-O2 | (2-8) | 20% |
| 3-HH1OB(2F,3F)-O2 | (2-8) | 14% |
| 3-HH-V | (3-1) | 29% |
| 1-BB-3 | (3-3) | 10% |
| 3-HHB-1 | (3-5) | 8% |
| 5-B(F)BB-2 | (3-7) | 6% |

NI = 74.5° C.; Tc < −20° C.; Δn = 0.106; Δε = −3.0; Vth = 2.21 V; η = 14.7 mPa · s.

To the composition, compound (1) was added in a proportion of 0.5% by weight, and VHR-11 was measured.
VHR-11=72.4%

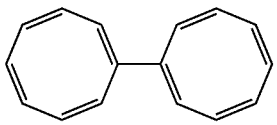

(1)

Comparative Example 1

To the composition in Example 1, compound (1) was not added, and VHR-11 was measured.
VHR-11=31.5%

Example 2

| | | |
|---|---|---|
| 3-HB(2F,3F)-O4 | (2-1) | 6% |
| 3-H2B(2F,3F)-O2 | (2-2) | 8% |
| 3-H1OB(2F,3F)-O2 | (2-3) | 5% |
| 3-BB(2F,3F)-O2 | (2-4) | 10% |
| 2-HHB(2F,3F)-O2 | (2-6) | 7% |
| 3-HHB(2F,3F)-O2 | (2-6) | 7% |
| 5-HHB(2F,3F)-O2 | (2-6) | 7% |
| 2-HBB(2F,3F)-O2 | (2-10) | 4% |
| 3-HBB(2F,3F)-O2 | (2-10) | 7% |
| 5-HBB(2F,3F)-O2 | (2-10) | 6% |
| 3-HH-V | (3-1) | 11% |
| 1-BB-3 | (3-3) | 6% |
| 3-HHB-1 | (3-5) | 4% |
| 3-HHB-O1 | (3-5) | 4% |
| 3-HBB-2 | (3-6) | 4% |
| 3-B(F)BB-2 | (3-7) | 4% |

NI = 87.6° C.; Tc < −20° C.; Δn = 0.126; Δε = −4.5; Vth = 2.21 V; η = 25.3 mPa · s.

To the composition, compound (1) was added in a proportion of 0.5% by weight, and VHR-11 was measured.
VHR-11=75.3%

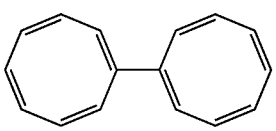

(1)

Example 3

| | | |
|---|---|---|
| 3-HB(2F,3F)-O2 | (2-1) | 5% |
| 5-HB(2F,3F)-O2 | (2-1) | 7% |
| 3-BB(2F,3F)-O2 | (2-4) | 8% |
| 3-HHB(2F,3F)-O2 | (2-6) | 5% |
| 5-HHB(2F,3F)-O2 | (2-6) | 4% |
| 3-HH1OB(2F,3F)-O2 | (2-8) | 5% |
| 2-BB(2F,3F)B-3 | (2-9) | 4% |
| 2-HBB(2F,3F)-O2 | (2-10) | 3% |
| 3-HBB(2F,3F)-O2 | (2-10) | 9% |
| 4-HBB(2F,3F)-O2 | (2-10) | 4% |
| 5-HBB(2F,3F)-O2 | (2-10) | 8% |
| 3-HH-V | (3-1) | 27% |
| 3-HH-V1 | (3-1) | 6% |
| V-HHB-1 | (3-5) | 5% |

NI = 81.2° C.; Tc < −20° C.; Δn = 0.107; Δε = −3.2; Vth = 2.11 V; η = 15.5 mPa · s.

To the composition, compound (1) was added in a proportion of 0.4% by weight, and VHR-11 was measured.
VHR-11=73.4%

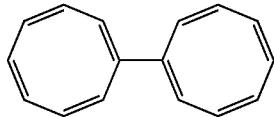
(1)

Example 4

| | | |
|---|---|---|
| 3-H2B(2F,3F)-O2 | (2-2) | 7% |
| 3-HHB(2F,3F)-O2 | (2-6) | 8% |
| 3-HH1OB(2F,3F)-O2 | (2-8) | 5% |
| 2-BB(2F,3F)B-3 | (2-9) | 7% |
| 2-BB(2F,3F)B-4 | (2-9) | 7% |
| 3-HDhB(2F,3F)-O2 | (2-16) | 3% |
| 5-HDhB(2F,3F)-O2 | (2-16) | 4% |
| 2-HchB(2F,3F)-O2 | (2-19) | 8% |
| 4-HH-V | (3-1) | 15% |
| 3-HH-V1 | (3-1) | 6% |
| 1-HH-2V1 | (3-1) | 6% |
| 3-HH-2V1 | (3-1) | 4% |
| V2-BB-1 | (3-3) | 5% |
| 1V2-BB-1 | (3-3) | 5% |
| 3-HHB-1 | (3-5) | 6% |
| 3-HB(F)BH-3 | (3-12) | 4% |

NI = 88.7° C.; Tc < −20° C.; Δn = 0.115; Δε = −1.9; Vth = 2.82 V; η = 17.3 mPa · s.

To the composition, compound (1) was added in a proportion of 0.5% by weight, and VHR-11 was measured.
VHR-11=73.8%

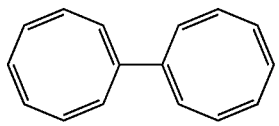
(1)

Example 5

| | | |
|---|---|---|
| V2-H2B(2F,3F)-O2 | (2-2) | 8% |
| V2-H1OB(2F,3F)-O4 | (2-3) | 4% |
| 3-BB(2F,3F)-O2 | (2-4) | 7% |
| 2-HHB(2F,3F)-O2 | (2-6) | 7% |
| 3-HHB(2F,3F)-O2 | (2-6) | 7% |
| 3-HH2B(2F,3F)-O2 | (2-7) | 7% |
| 5-HH2B(2F,3F)-O2 | (2-7) | 4% |
| V-HH2B(2F,3F)-O2 | (2-7) | 6% |
| V2-HBB(2F,3F)-O2 | (2-10) | 5% |
| V-HBB(2F,3F)-O2 | (2-10) | 5% |
| V-HBB(2F,3F)-O4 | (2-10) | 6% |
| 2-HH-3 | (3-1) | 12% |
| 1-BB-5 | (3-3) | 12% |
| 3-HHB-1 | (3-5) | 4% |
| 3-HHB-O1 | (3-5) | 3% |
| 3-HBB-2 | (3-6) | 3% |

NI = 89.9° C.; Tc <−20° C.; Δn = 0.122; Δε = −4.2; Vth = 2.16 V; η = 23.4 mPa · s.

To the composition, compound (1) was added in a proportion of 0.1% by weight, and VHR-11 was measured.
VHR-11=80.5%

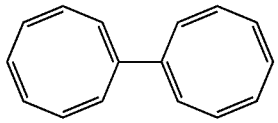
(1)

Example 6

| | | |
|---|---|---|
| 3-HB(2F,3F)-O2 | (2-1) | 3% |
| V-HB(2F,3F)-O2 | (2-1) | 3% |
| V2-HB (2F,3F)-O2 | (2-1) | 5% |
| 5-H2B(2F,3F)-O2 | (2-2) | 5% |
| V2-BB(2F,3F)-O2 | (2-4) | 3% |
| 1V2-BB(2F,3F)-O2 | (2-4) | 3% |
| 3-HHB(2F,3F)-O2 | (2-6) | 6% |
| V-HHB(2F,3F)-O2 | (2-6) | 6% |
| V-HHB(2F,3F)-O4 | (2-6) | 5% |
| V2-HHB(2F,3F)-O2 | (2-6) | 4% |
| V2-BB(2F,3F)B-1 | (2-9) | 4% |
| V2-HBB(2F,3F)-O2 | (2-10) | 5% |
| V-HBB(2F,3F)-O2 | (2-10) | 4% |
| V-HBB(2F,3F)-O4 | (2-10) | 5% |
| V-HHB(2F,3Cl)-O2 | (2-12) | 3% |
| 3-HH-V | (3-1) | 27% |
| 3-HH-V1 | (3-1) | 6% |
| V-HHB-1 | (3-5) | 3% |

NI = 77.1° C.; Tc <−20° C.; Δn = 0.101; Δε = −3.0; Vth = 2.04 V; η = 13.9 mPa · s.

To the composition, compound (1) was added in a proportion of 0.3% by weight, and VHR-11 was measured.
VHR-11=78.2%

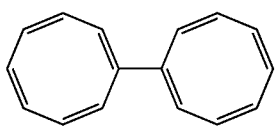
(1)

Example 7

| | | |
|---|---|---|
| 3-HB(2F,3F)-O4 | (2-1) | 6% |
| 3-H2B(2F,3F)-O2 | (2-2) | 8% |
| 3-H1OB(2F,3F)-O2 | (2-3) | 4% |
| 3-BB(2F,3F)-O2 | (2-4) | 7% |
| 2-HHB(2F,3F)-O2 | (2-6) | 6% |
| 3-HHB(2F,3F)-O2 | (2-6) | 10% |
| 5-HHB(2F,3F)-O2 | (2-6) | 8% |
| 2-HBB(2F,3F)-O2 | (2-10) | 5% |
| 3-HBB(2F,3F)-O2 | (2-10) | 7% |
| 5-HBB(2F,3F)-O2 | (2-10) | 5% |
| 2-HH-3 | (3-1) | 12% |
| 1-BB-3 | (3-3) | 6% |
| 3-HHB-1 | (3-5) | 3% |
| 3-HHB-O1 | (3-5) | 4% |
| 3-HBB-2 | (3-6) | 6% |
| 3-B(F)BB-2 | (3-7) | 3% |

NI = 93.0° C.; Tc <−20° C.; Δn = 0.124; Δε = −4.5; Vth = 2.22 V; η = 25.0 mPa · s.

To the composition, compound (1) was added in a proportion of 0.5% by weight, and VHR-11 was measured.
VHR-11=81.6%

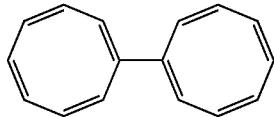
(1)

Example 8

| | | |
|---|---|---|
| V-HB(2F,3F)-O2 | (2-1) | 7% |
| V2-BB(2F,3F)-O2 | (2-4) | 10% |
| V-HHB(2F,3F)-O1 | (2-6) | 7% |
| V-HHB(2F,3F)-O2 | (2-6) | 9% |
| V2-HHB(2F,3F)-O2 | (2-6) | 8% |
| 3-HH2B(2F,3F)-O2 | (2-7) | 9% |
| V-HBB(2F,3F)-O2 | (2-10) | 8% |
| V-HBB(2F,3F)-O4 | (2-10) | 6% |
| 3-HH-V | (3-1) | 15% |
| 3-HH-V1 | (3-1) | 6% |
| 2-HH-3 | (3-1) | 9% |
| 3-HH-5 | (3-1) | 3% |
| 1V2-HH-3 | (3-1) | 3% |

NI = 87.5° C.; Tc <−20° C.; Δn = 0.100; Δε = −3.4; Vth = 2.02 V; η = 18.9 mPa · s.

To the composition, compound (1) was added in a proportion of 0.1% by weight, and VHR-11 was measured.
VHR-11=77.9%

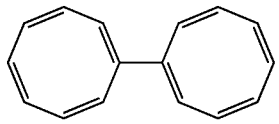
(1)

Example 9

| | | |
|---|---|---|
| 3-HB(2F,3F)-O2 | (2-1) | 7% |
| 5-HB(2F,3F)-O2 | (2-1) | 7% |
| 3-BB(2F,3F)-O2 | (2-4) | 8% |
| 3-HHB(2F,3F)-O2 | (2-6) | 4% |
| 5-HHB(2F,3F)-O2 | (2-6) | 5% |
| 3-HH1OB(2F,3F)-O2 | (2-8) | 5% |
| 2-BB(2F,3F)B-3 | (2-9) | 4% |
| 2-HBB(2F,3F)-O2 | (2-10) | 3% |
| 3-HBB(2F,3F)-O2 | (2-10) | 8% |
| 4-HBB(2F,3F)-O2 | (2-10) | 5% |
| 5-HBB(2F,3F)-O2 | (2-10) | 8% |
| 3-HH-V | (3-1) | 33% |
| V-HHB-1 | (3-5) | 3% |

NI = 76.4° C.; Tc <−20° C.; Δn = 0.104; Δε = −3.2; Vth = 2.06 V; η = 15.6 mPa · s.

To the composition, compound (1) was added in a proportion of 0.4% by weight, and VHR-11 was measured.
VHR-11=74.1%

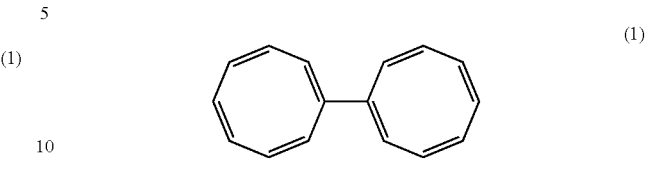
(1)

Example 10

| | | |
|---|---|---|
| 2-H1OB(2F,3F)-O2 | (2-3) | 6% |
| 3-H1OB(2F,3F)-O2 | (2-3) | 4% |
| 3-BB(2F,3F)-O2 | (2-4) | 3% |
| 2-HH1OB(2F,3F)-O2 | (2-8) | 14% |
| 2-HBB(2F,3F)-O2 | (2-10) | 7% |
| 3-HBB(2F,3F)-O2 | (2-10) | 11% |
| 5-HBB(2F,3F)-O2 | (2-10) | 9% |
| 2-HH-3 | (3-1) | 5% |
| 3-HH-VFF | (3-1) | 30% |
| 1-BB-3 | (3-3) | 5% |
| 3-HHB-1 | (3-5) | 3% |
| 3-HBB-2 | (3-6) | 3% |

NI = 78.3° C.; Tc <−20° C.; Δn = 0.103; Δε = −3.2; Vth = 2.17 V; η = 17.7 mPa · s.

To the composition, compound (1) was added in a proportion of 0.5% by weight, and VHR-11 was measured.
VHR-11=72.9%

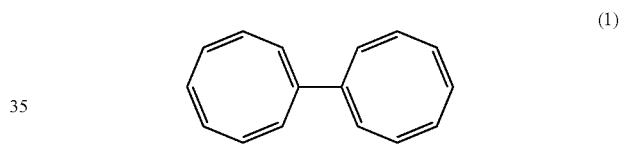
(1)

Example 11

| | | |
|---|---|---|
| V-HB(2F,3F)-O2 | (2-1) | 10% |
| V2-HB(2F,3F)-O2 | (2-1) | 10% |
| 2-H1OB(2F,3F)-O2 | (2-3) | 3% |
| 3-H1OB(2F,3F)-O2 | (2-3) | 3% |
| 2O-BB(2F,3F)-O2 | (2-4) | 3% |
| V2-BB(2F,3F)-O2 | (2-4) | 8% |
| V2-HHB(2F,3F)-O2 | (2-6) | 5% |
| 2-HBB(2F,3F)-O2 | (2-10) | 3% |
| 3-HBB(2F,3F)-O2 | (2-10) | 3% |
| V-HBB(2F,3F)-O2 | (2-10) | 6% |
| V-HBB(2F,3F)-O4 | (2-10) | 8% |
| V-HHB(2F,3Cl)-O2 | (2-12) | 7% |
| 3-HH-4 | (3-1) | 14% |
| V-HHB-1 | (3-5) | 10% |
| 3-HBB-2 | (3-6) | 7% |

NI = 75.9° C.; Tc <−20° C.; Δn = 0.114; Δε = −3.9; Vth = 2.20 V; η = 24.7 mPa · s.

To the composition, compound (1) was added in a proportion of 0.3% by weight, and VHR-11 was measured.
VHR-11=77.5%

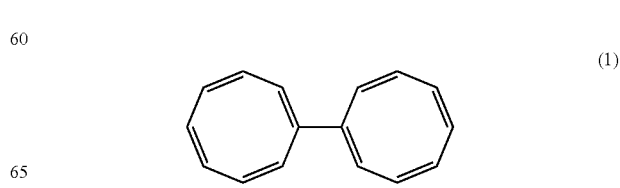
(1)

Example 12

| | | |
|---|---|---|
| 3-HB(2F,3F)-O2 | (2-1) | 10% |
| 5-HB(2F,3F)-O2 | (2-1) | 7% |
| 2-BB(2F,3F)-O2 | (2-4) | 7% |
| 3-BB(2F,3F)-O2 | (2-4) | 7% |
| 3-B(2F,3F)B(2F,3F)-O2 | (2-5) | 3% |
| 2-HHB(2F,3F)-O2 | (2-6) | 5% |
| 3-HHB(2F,3F)-O2 | (2-6) | 10% |
| 2-HBB(2F,3F)-O2 | (2-10) | 8% |
| 3-HBB(2F,3F)-O2 | (2-10) | 10% |
| 2-HH-3 | (3-1) | 14% |
| 3-HB-O1 | (3-2) | 5% |
| 3-HHB-1 | (3-5) | 3% |
| 3-HHB-O1 | (3-5) | 3% |
| 3-HHB-3 | (3-5) | 4% |
| 2-BB(F)B-3 | (3-8) | 4% |

NI = 73.2° C.; Tc <−20° C.; Δn = 0.113; Δε = −4.0; Vth = 2.18 V; η = 22.6 mPa · s.

To the composition, compound (1) was added in a proportion of 0.2% by weight, and VHR-11 was measured.
VHR-11=80.2%

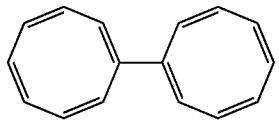

(1)

Example 13

| | | |
|---|---|---|
| 3-HB(2F,3F)-O4 | (2-1) | 6% |
| 3-H2B(2F,3F)-O2 | (2-2) | 8% |
| 3-H1OB(2F,3F)-O2 | (2-3) | 4% |
| 3-BB(2F,3F)-O2 | (2-4) | 7% |
| 2-HHB(2F,3F)-O2 | (2-6) | 7% |
| 3-HHB(2F,3F)-O2 | (2-6) | 7% |
| 3-HH2B(2F,3F)-O2 | (2-7) | 7% |
| 5-HH2B(2F,3F)-O2 | (2-7) | 4% |
| 2-HBB(2F,3F)-O2 | (2-10) | 5% |
| 3-HBB(2F,3F)-O2 | (2-10) | 5% |
| 4-HBB(2F,3F)-O2 | (2-10) | 6% |
| 2-HH-3 | (3-1) | 12% |
| 1-BB-5 | (3-3) | 12% |
| 3-HHB-1 | (3-5) | 4% |
| 3-HHB-O1 | (3-5) | 3% |
| 3-HBB-2 | (3-6) | 3% |

NI = 82.8° C.; Tc <−20° C.; Δn = 0.118; Δε = −4.4; Vth = 2.13 V; η = 22.5 mPa · s.

To the composition, compound (1) was added in a proportion of 0.08% by weight, and VHR-11 was measured.
VHR-11=77.6%

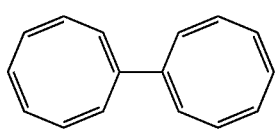

(1)

Example 14

| | | |
|---|---|---|
| 3-HB(2F,3F)-O2 | (2-1) | 7% |
| 5-HB(2F,3F)-O2 | (2-1) | 7% |
| 3-BB(2F,3F)-O2 | (2-4) | 8% |
| 3-HHB(2F,3F)-O2 | (2-6) | 5% |
| 5-HHB(2F,3F)-O2 | (2-6) | 4% |
| 3-HH1OB(2F,3F)-O2 | (2-8) | 4% |
| 2-BB(2F,3F)B-3 | (2-9) | 5% |
| 2-HBB(2F,3F)-O2 | (2-10) | 3% |
| 3-HBB(2F,3F)-O2 | (2-10) | 8% |
| 4-HBB(2F,3F)-O2 | (2-10) | 5% |
| 5-HBB(2F,3F)-O2 | (2-10) | 8% |
| 3-HH-V | (3-1) | 27% |
| 3-HH-V1 | (3-1) | 6% |
| V-HHB-1 | (3-5) | 3% |

NI = 78.1° C.; Tc <−20° C.; Δn = 0.107; Δε = −3.2; Vth = 2.02 V; η = 15.9 mPa · s.

To the composition, compound (1) was added in a proportion of 0.5% by weight, and VHR-11 was measured.
VHR-11=75.8%

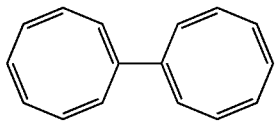

(1)

Example 15

| | | |
|---|---|---|
| 3-HB(2F,3F)-O2 | (2-1) | 10% |
| 5-HB(2F,3F)-O2 | (2-1) | 10% |
| 3-H2B(2F,3F)-O2 | (2-2) | 8% |
| 5-H2B(2F,3F)-O2 | (2-2) | 8% |
| 2-HBB(2F,3F)-O2 | (2-10) | 6% |
| 3-HBB(2F,3F)-O2 | (2-10) | 8% |
| 4-HBB(2F,3F)-O2 | (2-10) | 7% |
| 5-HBB(2F,3F)-O2 | (2-10) | 7% |
| 3-HDhB(2F,3F)-O2 | (2-16) | 5% |
| 3-HH-4 | (3-1) | 14% |
| V-HHB-1 | (3-5) | 10% |
| 3-HBB-2 | (3-6) | 7% |

NI = 88.5° C.; Tc <−20° C.; Δn = 0.108; Δε = −3.8; Vth = 2.25 V; η = 24.6 mPa · s.

To the composition, compound (1) was added in a proportion of 0.1% by weight, and VHR-11 was measured.
VHR-11=80.1%

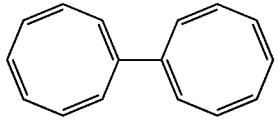

(1)

Example 16

| | | |
|---|---|---|
| 3-HB(2F,3F)-O2 | (2-1) | 7% |
| 3-HB(2F,3F)-O4 | (2-1) | 8% |
| 3-H2B(2F,3F)-O2 | (2-2) | 8% |
| 3-BB(2F,3F)-O2 | (2-4) | 10% |

-continued

| | | |
|---|---|---|
| 2-HHB(2F,3F)-O2 | (2-6) | 4% |
| 3-HHB(2F,3F)-O2 | (2-6) | 7% |
| 3-HHB(2F,3F)-1 | (2-6) | 6% |
| 2-HBB(2F,3F)-O2 | (2-10) | 6% |
| 3-HBB(2F,3F)-O2 | (2-10) | 6% |
| 4-HBB(2F,3F)-O2 | (2-10) | 5% |
| 5-HBB(2F,3F)-O2 | (2-10) | 4% |
| 3-HEB(2F,3F)B(2F,3F)-O2 | (2-11) | 3% |
| 3-H1OCro(7F,8F)-5 | (2-14) | 3% |
| 3-HDhB(2F,3F)-O2 | (2-16) | 5% |
| 3-HH-O1 | (3-1) | 5% |
| 1-BB-5 | (3-3) | 4% |
| V-HHB-1 | (3-5) | 4% |
| 5-HB(F)BH-3 | (3-12) | 5% |

NI = 81.1° C.; Tc <−20° C.; Δn = 0.119; Δε = −4.5; Vth = 1.69 V; η = 31.4 mPa · s.

To the composition, compound (1) was added in a proportion of 0.3% by weight, and VHR-11 was measured. VHR-11=79.7%

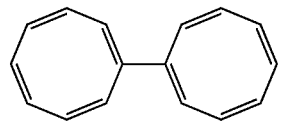

(1)

Example 17

| | | |
|---|---|---|
| 3-HB(2F,3F)-O4 | (2-1) | 15% |
| 3-HBB(2F,3F)-O2 | (2-10) | 8% |
| 4-HBB(2F,3F)-O2 | (2-10) | 5% |
| 5-HBB(2F,3F)-O2 | (2-10) | 7% |
| 3-dhBB(2F,3F)-O2 | (2-17) | 5% |
| 3-chB(2F,3F)-O2 | (2-18) | 7% |
| 2-HchB(2F,3F)-O2 | (2-19) | 8% |
| 5-HH-V | (3-1) | 18% |
| 7-HB-1 | (3-2) | 5% |
| V-HHB-1 | (3-5) | 7% |
| V2-HHB-1 | (3-5) | 7% |
| 3-HBB(F)B-3 | (3-13) | 8% |

NI = 98.8° C.; Tc <−20° C.; Δn = 0.111; Δε = −3.2; Vth = 2.47 V; η = 23.9 mPa · s.

To the composition, compound (1) was added in a proportion of 0.5% by weight, and VHR-11 was measured. VHR-11=78.9%

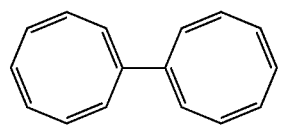

(1)

Example 18

| | | |
|---|---|---|
| 3-H2B(2F,3F)-O2 | (2-2) | 18% |
| 5-H2B(2F,3F)-O2 | (2-2) | 17% |
| 3-HHB(2F,3Cl)-O2 | (2-12) | 5% |
| 3-HBB(2F,3Cl)-O2 | (2-13) | 8% |
| 5-HBB(2F,3Cl)-O2 | (2-13) | 7% |
| 3-HDhB(2F,3F)-O2 | (2-16) | 5% |
| 3-HH-V | (3-1) | 11% |
| 3-HH-VFF | (3-1) | 7% |
| F3-HH-V | (3-1) | 10% |
| 3-HHEH-3 | (3-4) | 4% |
| 3-HB(F)HH-2 | (3-10) | 4% |
| 3-HHEBH-3 | (3-11) | 4% |

NI = 77.5° C.; Tc <−20° C.; Δn = 0.084; Δε = −2.6; Vth = 2.43 V; η = 22.8 mPa · s.

To the composition, compound (1) was added in a proportion of 0.4% by weight, and VHR-11 was measured. VHR-11=80.8%

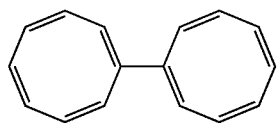

(1)

Example 19

| | | |
|---|---|---|
| 3-HB(2F,3F)-O2 | (2-1) | 8% |
| 3-H2B(2F,3F)-O2 | (2-2) | 10% |
| 3-BB(2F,3F)-O2 | (2-4) | 10% |
| 2O-BB(2F,3F)-O2 | (2-4) | 3% |
| 2-HHB(2F,3F)-O2 | (2-6) | 4% |
| 3-HHB(2F,3F)-O2 | (2-6) | 7% |
| 2-HHB(2F,3F)-1 | (2-6) | 5% |
| 2-BB(2F,3F)B-3 | (2-9) | 6% |
| 2-BB(2F,3F)B-4 | (2-9) | 6% |
| 2-HBB(2F,3F)-O2 | (2-10) | 4% |
| 3-HBB(2F,3F)-O2 | (2-10) | 7% |
| 3-HH1OCro(7F,8F)-5 | (2-15) | 4% |
| 3-HDhB(2F,3F)-O2 | (2-16) | 6% |
| 3-dhBB(2F,3F)-O2 | (2-17) | 4% |
| 3-HH-V | (3-1) | 11% |
| 1-BB-5 | (3-3) | 5% |

NI = 70.6° C.; Tc <−20° C.; Δn = 0.129; Δε = −4.3; Vth = 1.69 V; η = 27.0 mPa · s.

To the composition, compound (1) was added in a proportion of 0.5% by weight, and VHR-11 was measured. VHR-11=76.1%

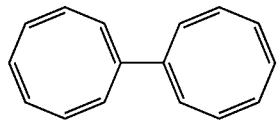

(1)

The voltage holding ratio (VHR-11) of the composition after the device was irradiated with ultraviolet light in Comparative Example 1 was 31.5%. In contrast, the VHR-11 of the composition in Example 1 was 72.4%. Thus, the composition in Example 1 had larger VHR-11 in comparison with the composition in Comparative Example 1. Accordingly, the liquid crystal composition according to the invention is concluded to have superb characteristics.

INDUSTRIAL APPLICABILITY

A liquid crystal composition according to the invention can be used in a liquid crystal monitor, a liquid crystal television and so forth.

What is claimed is:

1. A liquid crystal composition that contains a compound represented by formula (1) as a first additive and at least one compound represented by formula (2) as a first component, and has a nematic phase and negative dielectric anisotropy:

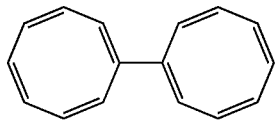
(1)

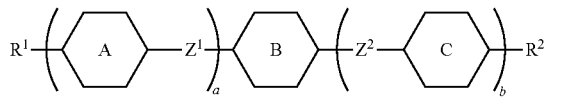
(2)

wherein, in formula (2), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen is replaced by fluorine or chlorine; ring A and ring C are independently 1,4-cyclohexylene, 1,4-cyclohexenylene, 1,4-phenylene, 1,4-phenylene in which at least one hydrogen is replaced by fluorine or chlorine, or tetrahydropyran-2,5-diyl; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^1$ and $Z^2$ are independently a single bond, ethylene, methyleneoxy or carbonyloxy; a is 1, 2 or 3, and b is 0 or 1; and a sum of a and b is 3 or less.

2. The liquid crystal composition according to claim 1, wherein a proportion of the first additive is in the range of 0.005% by weight to 2% by weight.

3. The liquid crystal composition according to claim 1, containing at least one compound selected from the group of compounds represented by formula (2-1) to formula (2-22) as the first component:

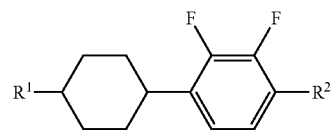
(2-1)

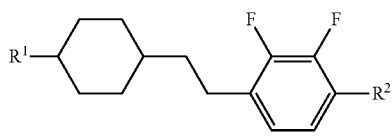
(2-2)

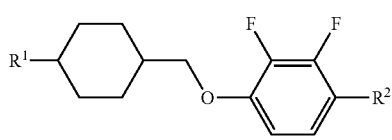
(2-3)

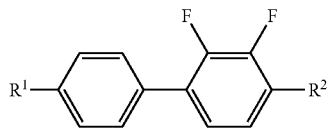
(2-4)

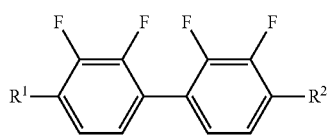
(2-5)

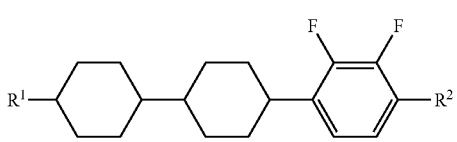
(2-6)

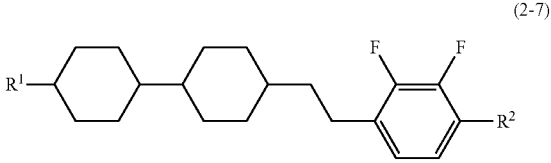
(2-7)

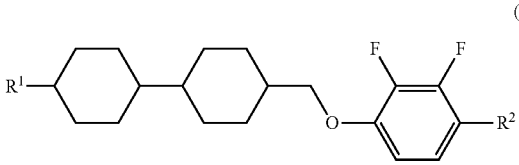
(2-8)

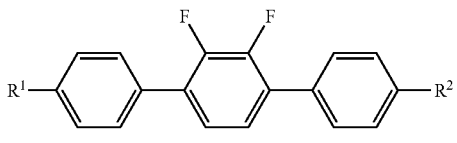
(2-9)

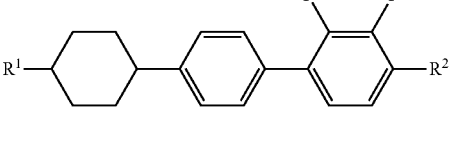
(2-10)

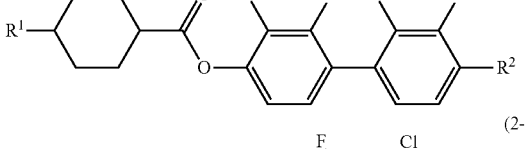
(2-11)

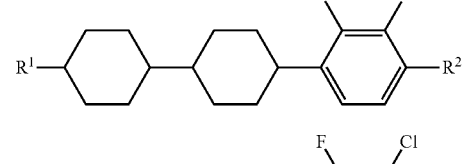
(2-12)

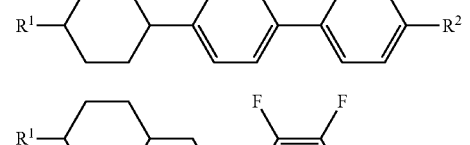
(2-13)

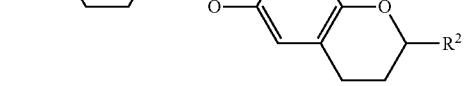
(2-14)

-continued

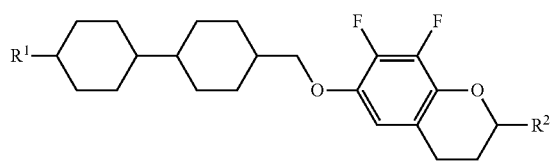
(2-15)

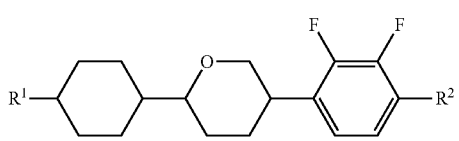
(2-16)

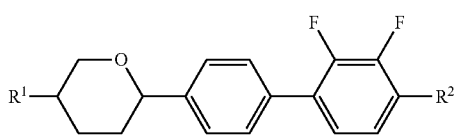
(2-17)

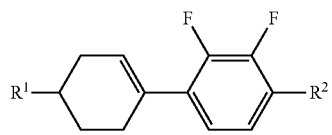
(2-18)

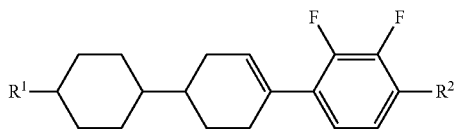
(2-19)

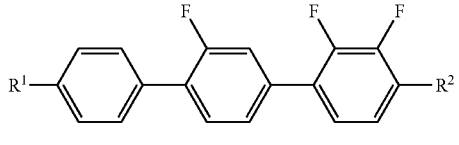
(2-20)

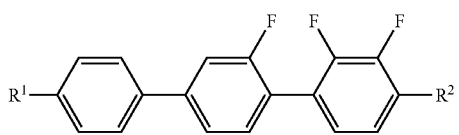
(2-21)

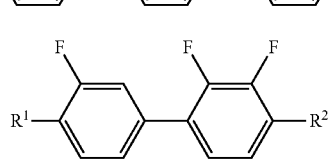
(2-22)

wherein, in formula (2-1) to formula (2-22), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen is replaced by fluorine or chlorine.

4. The liquid crystal composition according to claim 1, wherein a proportion of the first component is in the range of 10% by weight to 90% by weight.

5. The liquid crystal composition according to claim 1, containing at least one compound represented by formula (3) as a second component:

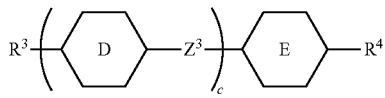
(3)

wherein, in formula (3), $R^3$ and $R^4$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine or chlorine; ring D and ring E are independently 1,4-cyclohexylene, 1,4-phenylene, 2-fluoro-1,4-phenylene or 2,5-difluoro-1,4-phenylene; $Z^3$ is a single bond, ethylene or carbonyloxy; and c is 1, 2 or 3.

6. The liquid crystal composition according to claim 5, containing at least one compound selected from the group of compounds represented by formula (3-1) to formula (3-13) as the second component:

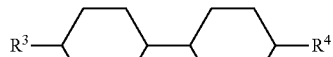
(3-1)

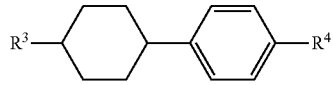
(3-2)

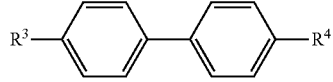
(3-3)

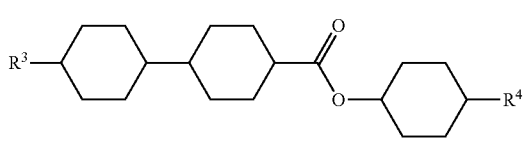
(3-4)

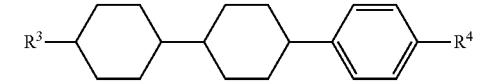
(3-5)

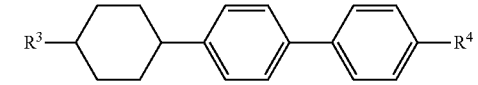
(3-6)

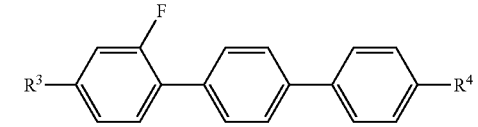
(3-7)

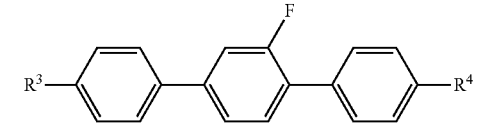
(3-8)

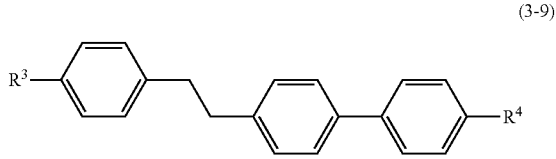
(3-9)

-continued (3-10)
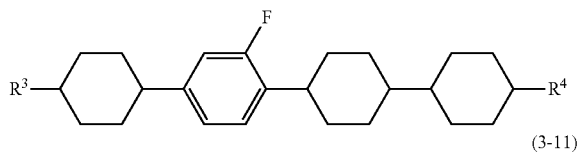

(3-11)
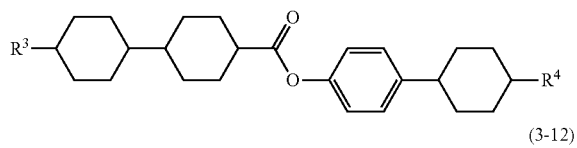

(3-12)
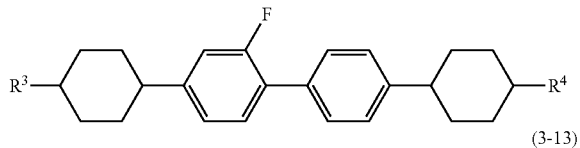

(3-13)
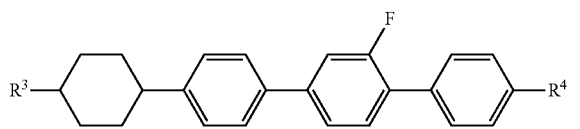

wherein, in formula (3-1) to formula (3-13), $R^3$ and $R^4$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine or chlorine.

7. The liquid crystal composition according to claim 5, wherein a proportion of the second component is in the range of 10% by weight to 90% by weight.

8. The liquid crystal composition according to claim 1, containing at least one compound represented by formula (4) as a second additive:

(4)
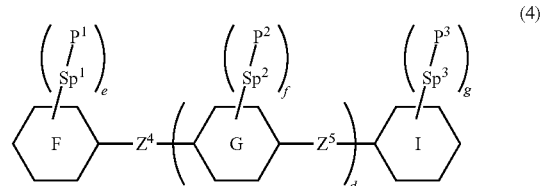

wherein, in formula (4), ring F and ring I are independently cyclohexyl, cyclohexenyl, phenyl, 1-naphthyl, 2-naphthyl, tetrahydropyran-2-yl or 1,3-dioxane-2-yl, pyrimidine-2-yl or pyridine-2-yl, and in the rings, at least one hydrogen may be replaced by fluorine, chlorine, alkyl having 1 to 12 carbons, alkoxy having 1 to 12 carbons, or alkyl having 1 to 12 carbons in which one hydrogen is replaced by fluorine or chlorine; ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by fluorine, chlorine, alkyl having 1 to 12 carbons, alkoxy having 1 to 12 carbons, or alkyl having 1 to 12 carbons in which at least one hydrogen is replaced by fluorine or chlorine; $Z^4$ and $Z^5$ are independently a single bond or alkylene having 1 to 10 carbons, and in the alkylene, at least one —CH$_2$— may be replaced by —O—, —CO—, —COO— or —OCO—, and at least one —CH$_2$—CH$_2$— may be replaced by —CH=CH—, —C(CH$_3$)=CH—, —CH=C(CH$_3$)— or —C(CH$_3$)=C(CH$_3$)—, and in these groups, at least one hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one —CH$_2$— may be replaced by —O—, —COO—, —OCO— or —OCOO—, and at least one —CH$_2$—CH$_2$— may be replaced by —CH=CH— or —C≡C—, and in these groups, at least one hydrogen may be replaced by fluorine or chlorine; d is 0, 1 or 2; e, f and g are independently 0, 1, 2, 3 or 4; and a sum of e, f and g is 1 or more.

9. The liquid crystal composition according to claim 8, wherein, in formula (4), $P^1$, $P^2$ and $P^3$ are independently a group selected from the group of polymerizable groups represented by formula (P-1) to formula (P-5):

(P-1)
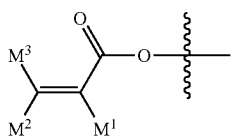

(P-2)
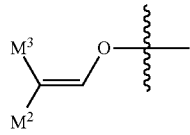

(P-3)
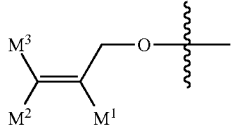

(P-4)
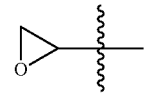

(P-5)
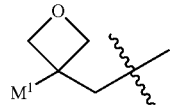

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one hydrogen is replaced by fluorine or chlorine.

10. The liquid crystal composition according to claim 8, containing at least one compound selected from the group of polymerizable compounds represented by formula (4-1) to formula (4-27) as the second additive:

(4-1) 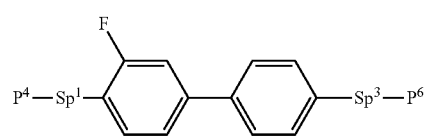
(4-2) 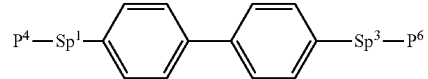
(4-3) 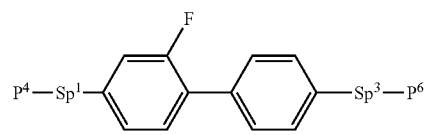
(4-4) 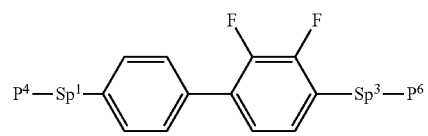
(4-5) 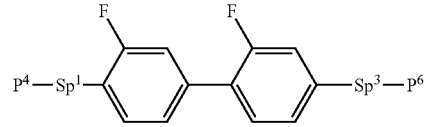
(4-6) 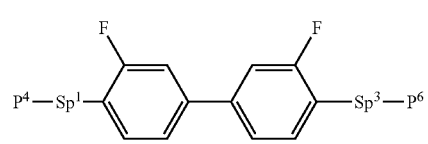
(4-7) 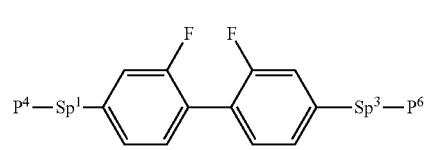
(4-8) 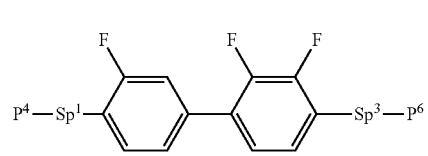
(4-9) 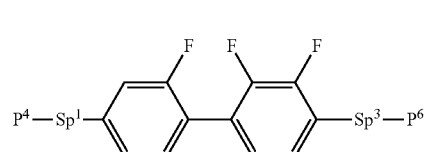
(4-10) 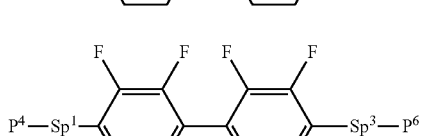
(4-11) 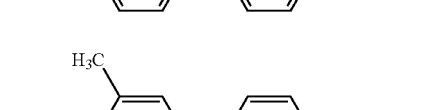
-continued
(4-12) 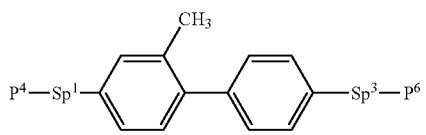
(4-13) 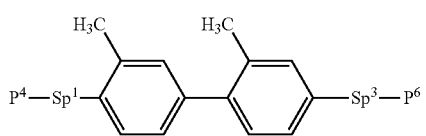
(4-14) 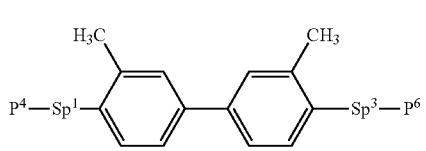
(4-15) 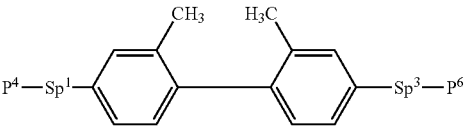
(4-16) 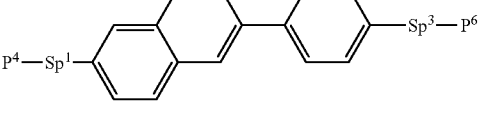
(4-17) 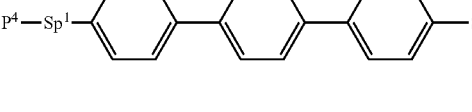
(4-18) 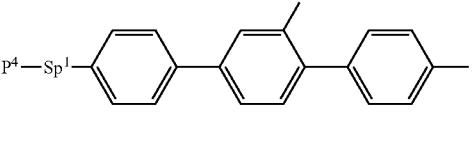
(4-19) 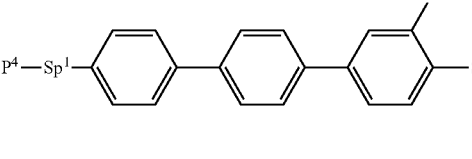
(4-20) 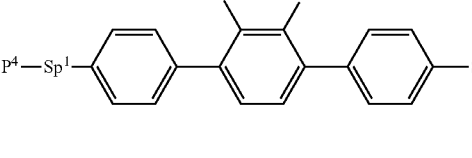
(4-21) 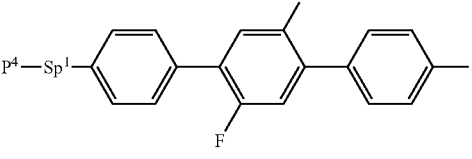

-continued (4-22) 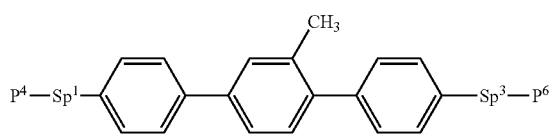

(4-23) 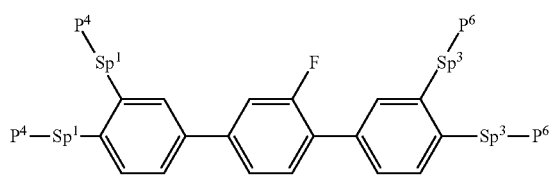

(4-24) 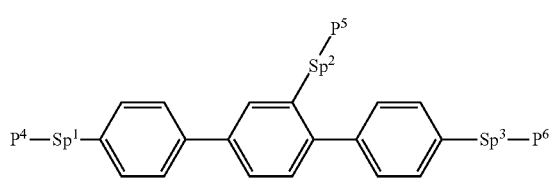

(4-25) 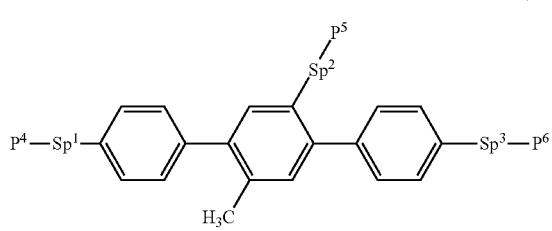

(4-26)

(4-27) 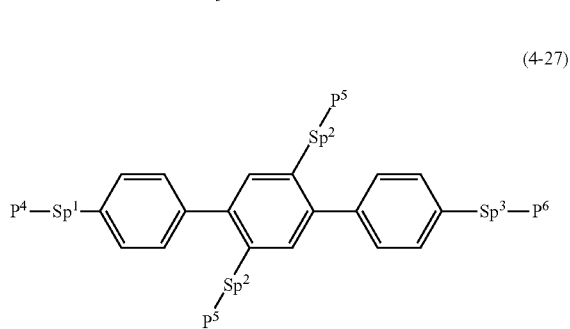

wherein, in formula (4-1) to formula (4-27), $P^4$, $P^5$ and $P^6$ are independently a polymerizable group selected from the group of groups represented by formula (P-1) to formula (P-3), in which $M^1$, $M^2$ and $M^3$ are independently hydrogen, fluorine, alkyl having 1 to 5 carbons, or alkyl having 1 to 5 carbons in which at least one hydrogen is replaced by fluorine or chlorine:

(P-1) 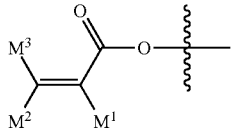

(P-2) 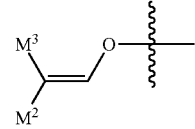

(P-3) 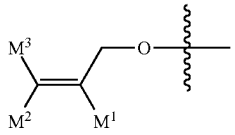

wherein, $Sp^1$, $Sp^2$ and $Sp^3$ are independently a single bond or alkylene having 1 to 10 carbons, and in the alkylene, at least one —CH$_2$— may be replaced by —O—, —COO—, —OCO— or —OCOO—, and at least one —CH$_2$—CH$_2$— may be replaced by —CH=CH— or —C≡C—, and in these groups, at least one hydrogen may be replaced by fluorine or chlorine.

11. The liquid crystal composition according to claim 8, wherein a proportion of the second additive is in the range of 0.03% by weight to 10% by weight.

12. A liquid crystal display device, including the liquid crystal composition according to claim 1.

13. The liquid crystal display device according to claim 12, wherein an operating mode in the liquid crystal display device includes an IPS mode, a VA mode, an FFS mode or an FPA mode, and a driving mode in the liquid crystal display device includes an active matrix mode.

14. A polymer sustained alignment mode liquid crystal display device, wherein the liquid crystal display device includes the liquid crystal composition according to claim 8, and a polymerizable compound in the liquid crystal composition is polymerized.

15. The liquid crystal composition according to claim 5, containing at least one compound represented by formula (4) as a second additive:

(4) 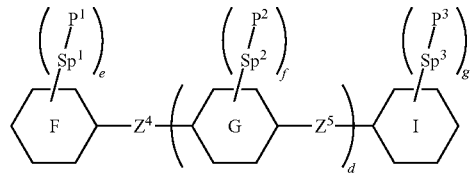

wherein, in formula (4), ring F and ring I are independently cyclohexyl, cyclohexenyl, phenyl, 1-naphthyl, 2-naphthyl, tetrahydropyran-2-yl or 1,3-dioxane-2-yl, pyrimidine-2-yl or pyridine-2-yl, and in the rings, at least one hydrogen may be replaced by fluorine, chlorine, alkyl having 1 to 12 carbons, alkoxy having 1 to 12 carbons, or alkyl having 1 to 12 carbons in which one hydrogen is replaced by fluorine or chlorine; ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by fluorine, chlorine, alkyl having 1 to 12 carbons, alkoxy having 1 to 12 carbons, or alkyl having 1 to 12 carbons in which at least one hydrogen is replaced by fluorine or chlorine; $Z^4$ and $Z^5$ are independently a single bond or alkylene having 1 to 10 carbons, and in the alkylene, at least one —$CH_2$— may be replaced by —O—, —CO—, —COO— or —OCO—, and at least one —$CH_2$—$CH_2$— may be replaced by —CH═CH—, —C($CH_3$)═CH—, —CH═C($CH_3$)— or —C($CH_3$)═C($CH_3$)—, and in these groups, at least one hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one piece of —$CH_2$— may be replaced by —O—, —COO—, —OCO— or —OCOO—, and at least one piece of —$CH_2$—$CH_2$— may be replaced by —CH═CH— or —C≡C—, and in these groups, at least one hydrogen may be replaced by fluorine or chlorine; d is 0, 1 or 2; e, f and g are independently 0, 1, 2, 3 or 4; and a sum of e, f and g is 1 or more.

\* \* \* \* \*